United States Patent
Harvey et al.

(10) Patent No.: US 9,956,198 B2
(45) Date of Patent: May 1, 2018

(54) **FURO[3,4-*B*]PYRAN COMPOUNDS AND PHARMACEUTICAL USES**

(71) Applicant: Victoria Link Limited, Kelburn, Wellington (NZ)

(72) Inventors: Joanne Elizabeth Harvey, Kelburn (NZ); Russell James Hewitt, Singapore (SG); Rathnayake Mudiyanselage Kalpani Kumari Somarathne, Kelburn (NZ)

(73) Assignee: Victoria Link Limited, Wellington (NZ)

(*) Notice: Subject to any disclaimer, the term of this patent is extended or adjusted under 35 U.S.C. 154(b) by 0 days. days.

(21) Appl. No.: 15/377,737

(22) Filed: Dec. 13, 2016

(65) Prior Publication Data

US 2017/0087124 A1    Mar. 30, 2017

Related U.S. Application Data

(62) Division of application No. 15/101,059, filed as application No. PCT/NZ2014/000237 on Dec. 1, 2014, now Pat. No. 9,556,194.

(30) Foreign Application Priority Data

Dec. 2, 2013 (NZ) ........................ 618489

(51) Int. Cl.
*C07D 493/04* (2006.01)
*A61K 31/35* (2006.01)

(52) U.S. Cl.
CPC .................... *A61K 31/35* (2013.01)

(58) Field of Classification Search
CPC ....... C07D 493/04; A61K 31/35; A61P 35/00; A61P 19/00
See application file for complete search history.

(56) References Cited

FOREIGN PATENT DOCUMENTS

JP    H10287679 A    10/1998
WO    WO-2012/092168 A1    7/2012

OTHER PUBLICATIONS

El-Elimat.T et al., Waol A, trans-dihydrowaol A, and cis-dihydrowaol A: polyketide-derived γ-lactones from a *Volutella* species, Tetrahedron Letters, vol. 54, (2013), pp. 4300-4302 Abstract, compounds 1-3 (figure 1).

Li.J et al., α-Pyrones and Pyranes from the Plant Pathogenic Fungus *Pestalotiopsis scirpina*, European Journal of Organic Chemistry, (2012), pp. 2445-2452 Abstract, compounds 4 and 5 (figure 1) Abstract, compounds 4 and 5 (figure 1).

Gao.X et al., Syntheses of (−)-TAN-2483A, (−)-Massarilactone B, and the Fusidilactone B Ring System. Revision of the Structures of and Syntheses of (±)-Waol A (FD-211) and (±)-Waol B (FD- 212), Journal of Organic Chemistry, vol. 69, (2004), pp. 5517-5527 Abstract, compounds TAN-2483A and TAN-2483B (figure 2) Abstract, compounds TAN-2483A and TAN-2483B (figure 2).

International Search Report and the Written Opinion of the International Searching Authority, PCT/NZ2014/000237.

Guo et al, Journal of Organic Chemistry, 2004, vol. 69, pp. 5517-5527.

*Primary Examiner* — Sudhakar Katakam
(74) *Attorney, Agent, or Firm* — Polsinelli PC

(57) ABSTRACT

Furo[3,4-b]pyran compounds similar in chemical structure to the natural product known as TAN-2483B and their use for treating cancer, osteoporosis, Type 2 diabetes, or immune diseases.

7 Claims, No Drawings

FURO[3,4-B]PYRAN COMPOUNDS AND PHARMACEUTICAL USES

CROSS-REFERENCE TO RELATED APPLICATIONS

This application is a divisional of U.S. application Ser. No. 15/101,059, filed on Jun. 2, 2016. U.S. application Ser. No. 15/101,059 is a national stage application (under 35 U.S.C. § 371) of PCT/NZ2014/000237, filed Dec. 1, 2014, which claims benefit of New Zealand Application No. 618489, filed Dec. 2, 2013, which are incorporated herein by reference in their entireties.

TECHNICAL FIELD

The invention relates to compounds that are structurally related to known biologically active natural products. The invention further relates to pharmaceutical compositions containing the compounds and to the use of the compounds for treating diseases. In particular, the invention relates to furo[3,4-b]pyran compounds similar in chemical structure to the natural product known as TAN-2483B.

BACKGROUND OF THE INVENTION

Chemical compounds that occur in nature have been an enormously valuable source of potential therapeutic agents for the treatment of many diseases. Following isolation from their source and purification, naturally occurring compounds may be used as active ingredients in pharmaceutical compositions. However, more commonly, derivatives or structural analogues of naturally occurring compounds become the active ingredients of pharmaceutical compositions. Although there are many instances of successful therapeutic treatments based on naturally occurring compounds, there remains a constant ongoing need for new and improved medicines. The search for natural products that may assist therefore continues.

Following the discovery of a class of compounds in which at least some members have potentially useful biological activity, there is usually a strong interest in the production of selected compounds from the class, initially for further development and ultimately for production on a large scale for marketing and sales. Production may be possible by simple isolation from a natural source, but typically this is not possible and synthetic or semi-synthetic processes are required to make sufficient quantities of the useful compounds.

One class of chemical compounds that has proven to be a rich source of compounds having biological activity is the furo[3,4-b]pyrans. Bioactive natural products incorporating the furo[3,4-b]pyran-5-one bicyclic system have been isolated from a variety of fungal sources. Fusidilactones A, B, D and E,[1,2] massarilactones B and D,[3-5] TAN-2483A and TAN-2483B,[6] and waol A[7-11] all contain this ring system. These fungal secondary metabolites display a variety of bioactivities, ranging from antibacterial to anti-tumour properties.

Syntheses of some members of the furo[3,4-b]pyran family of natural products, namely (−)-TAN-2483A, massarilactone B and waol A, are known.[9-11] These natural products either incorporate a degree of unsaturation across the fused 4a-7a bond (e.g. massarilactone B and fusidilactone A) or possess a cis-relationship between H-2 and H-7a (e.g. (−)-TAN-2483A and waol A). In contrast to the other members of this family, (−)-TAN-2483B, isolated from a Japanese filamentous fungus,[6] has a trans-relationship between H-2 and H-7a, and therefore presents different synthetic challenges.

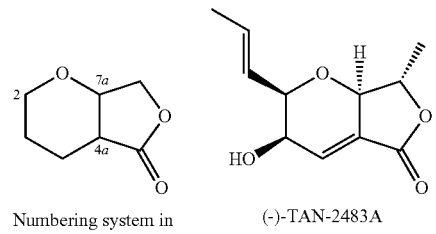

Numbering system in furo[3,4-b]pyran-5-ones (−)-TAN-2483A

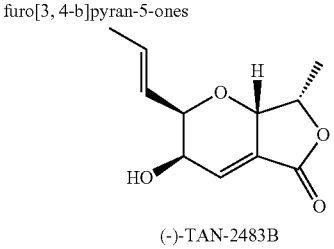

(−)-TAN-2483B (−)-TAN-2483A and (−)-TAN-2483B, isolated from fermentation of the filamentous fungus NR2329 (FERM BP-5905) in a culture medium, exhibit inhibition of c-Src (sarcoma) kinase and PTH-induced bone resorption. Therefore they have potential relevance to human pharmaceutics, including in cancer therapy and osteoporosis prevention or treatment. The synthesis of the furo[3,4-b]pyran core of (−)-TAN-2483B has been reported.[12] The synthetic route is via a D-mannose-derived cyclopropane key intermediate. Employing this general synthetic methodology, the inventors have investigated the synthesis of analogues of (−)-TAN-2483B with the objective of then determining their biological activities in a range of assays and assessing their potential as pharmaceutical agents for treating certain diseases. The inventors have now found that analogues of (−)-TAN-2483B show inhibitory activity against a range of kinase enzymes and also inhibit the growth of certain cancer cell lines.

It is therefore an object of the invention to provide novel compounds and their use for treating diseases, or to at least provide a useful alternative to existing pharmaceutical treatments.

SUMMARY OF THE INVENTION

In a first aspect of the invention there is provided a compound of the formula:

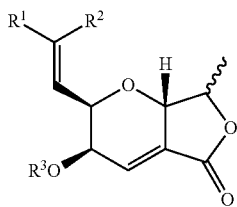

wherein $R^1$ and $R^2$ may each be H, $C_1$-$C_6$ alkyl, $C_1$-$C_6$ alkoxy, $C_2$-$C_6$ alkenyl, $C_2$-$C_6$ alkynyl, aryl, $CO_2H$, $CO_2$alkyl, or C(=O)alkyl, wherein each alkyl, alkoxy, alkenyl, alkynyl or aryl group may optionally be substituted with OH, $NH_2$, halogen, alkoxy, acyloxy or aryl; and $R^3$ is H, $C_1$-$C_6$ alkyl, $C_1$-$C_6$ acyl, aryl, benzyl or trialkylsilyl;

provided that R' is not $CH_3$ when $R^2$ and $R^3$ are both H or when $R^2$ is H and $R^3$ is acetyl;

or a pharmaceutically acceptable salt thereof.

In a second aspect of the invention there is provided a pharmaceutical composition comprising a compound of the invention and a pharmaceutically acceptable carrier.

In another aspect of the invention there is provided a method of treating cancer, osteoporosis, Type 2 diabetes or an immune disease comprising administering a pharmaceutically effective amount of a compound of the invention to a patient requiring treatment.

DETAILED DESCRIPTION

Definitions

The term "alkyl" means any saturated hydrocarbon radical, and is intended to include both straight- and branched-chain alkyl groups. Examples of alkyl groups include: methyl, ethyl, n-propyl, iso-propyl, n-butyl, iso-butyl, sec-butyl, t-butyl, n-pentyl, 1,1-dimethylpropyl, 1,2-dimethylpropyl, 2,2-dimethylpropyl, 1-ethylpropyl, 2-ethylpropyl, n-hexyl and 1-methyl-2-ethylpropyl.

The term "alkenyl" means any hydrocarbon radical having at least one double bond, and is intended to include both straight- and branched-chain alkenyl groups. Examples of alkenyl groups include: ethenyl, n-propenyl, iso-propenyl, n-butenyl, iso-butenyl, sec-butenyl, t-butenyl, n-pentenyl, 1,1-dimethylpropenyl, 1,2-dimethylpropenyl, 2,2-dimethylpropenyl, 1-ethylpropenyl, 2-ethylpropenyl, n-hexenyl and 1-methyl-2-ethyl propenyl.

The term "alkynyl" means any hydrocarbon radical having at least one carbon-carbon triple bond, and is intended to include both straight- and branched-chain alkynyl groups. Examples of alkynyl groups include: ethynyl, n-propynyl and n-butynyl.

The term "aryl" means an aromatic radical having 4 to 18 carbon atoms and includes heteroaromatic radicals. Examples include monocyclic groups, as well as fused groups such as bicyclic groups and tricyclic groups. Examples include phenyl, indenyl, 1-naphthyl, 2-naphthyl, azulenyl, heptalenyl, biphenyl, indacenyl, acenaphthyl, fluorenyl, phenalenyl, phenanthrenyl, anthracenyl, cyclopenta-cyclooctenyl, and benzocyclooctenyl, pyridyl, pyrrolyl, pyridazinyl, pyrimidinyl, pyrazinyl, triazolyl, and tetrazolyl.

The term "alkoxy" means an OR group, where R is alkyl as defined above.

The term "acyl" means a —(C═O)R group, where R is alkyl as defined above.

The term "acyloxy" means a —O(C═O)R group, where R is alkyl as defined above.

The term "pharmaceutically acceptable salt" is intended to apply to non-toxic salts derived from inorganic or organic acids, including, for example, the following acid salts: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, p-toluenesulfonate, salicylate, succinate, sulfate, tartrate, thiocyanate and undecanoate.

The "$\sim\sim\sim$" in the compound formula means that the methyl group attached to the furan ring at the position adjacent to the furan ring oxygen atom maybe in either the α- or β-stereochemistry.

Compounds of the Invention and Their Uses

The invention relates to compounds of the formula:

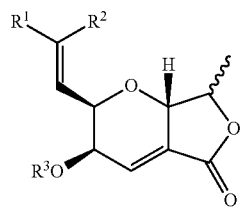

wherein $R^1$ and $R^2$ may each be H, $C_1$-$C_6$ alkyl, $C_1$-$C_6$ alkoxy, $C_2$-$C_6$ alkenyl, $C_2$-$C_6$ alkynyl, aryl, $CO_2H$, $CO_2$alkyl, or C(═O)alkyl, wherein each alkyl, alkoxy, alkenyl, alkynyl or aryl group may optionally be substituted with OH, $NH_2$, halogen, alkoxy, acyloxy or aryl; and $R^3$ is H, $C_1$-$C_6$ alkyl, $C_1$-$C_6$ acyl, aryl, benzyl or trialkylsilyl;

provided that $R^1$ is not $CH_3$ when $R^2$ and $R^3$ are both H or when $R^2$ is H and $R^3$ is acetyl;

or a pharmaceutically acceptable salt thereof.

In some embodiments of the invention, $R^1$ and $R^2$ may each be H, $C_1$-$C_6$ alkyl, $C_1$-$C_6$ alkoxy, $C_2$-$C_6$ alkenyl, $C_2$-$C_6$ alkynyl, aryl, $CO_2H$, $CO_2$alkyl, or C(═O)alkyl, wherein each alkyl, alkoxy, alkenyl, alkynyl or aryl group may optionally be substituted with OH, $NH_2$, halogen, or aryl; and $R^3$ is H, $C_1$-$C_6$ alkyl, aryl, benzyl or trialkylsilyl.

In some embodiments of the invention, one of $R^1$ and $R^2$ is $C_1$-$C_6$ alkyl and the other is H. For example, $R^1$ may be $C_1$-$C_6$ alkyl and $R^2$ is H. In other embodiments, one of $R^1$ and $R^2$ is $CH_2OH$ and the other is H. Thus, $R^1$ may be H and $R^2$ is $CH_2OH$, or $R^1$ may be $CH_2OH$ and $R^2$ is H. In other embodiments, one of $R^1$ and $R^2$ is $CO_2$alkyl and the other is H. For example, one of $R^1$ and $R^2$ may be $CO_2Et$. Thus, $R^1$ may be H and $R^2$ is $CO_2Et$, or $R^1$ may be $CO_2Et$ and $R^2$ is H. In further embodiments of the invention, one of $R^1$ and $R^2$ is $CO_2H$ and the other is H. In this case, $R^1$ may be H and $R^2$ is $CO_2H$, or $R^1$ may be $CO_2H$ and $R^2$ is H. In yet further embodiments of the invention, one of $R^1$ and $R^2$ may be Me, Et, $CH_2OMe$, or $CH_2OAc$.

In some embodiments of the invention, $R^3$ is H. Alternatively, $R^3$ may be alkyl, for example methyl or ethyl, or $R^3$ may be acetyl.

Preferred compounds of the invention include:

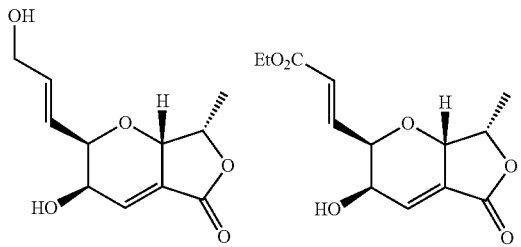

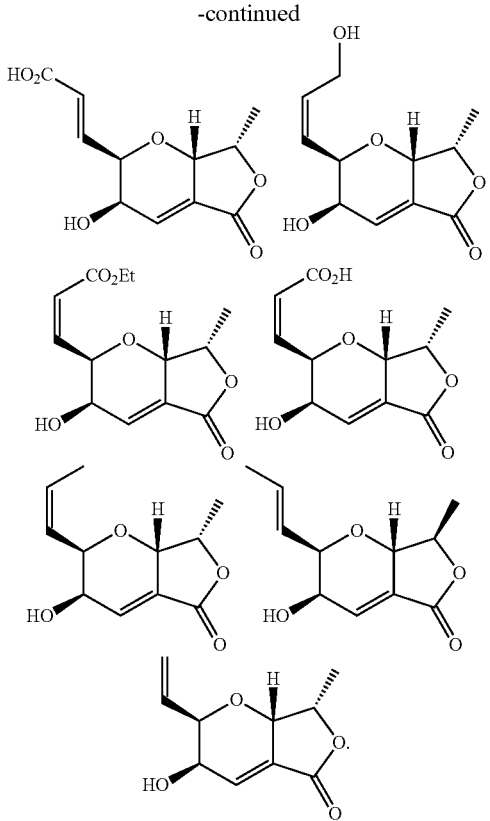

The invention also relates to a pharmaceutical composition comprising a compound of the invention and a pharmaceutically acceptable carrier. In another aspect, the invention relates to a method of treating cancer, osteoporosis, Type 2 diabetes, or an immune disease comprising administering a pharmaceutically effective amount of a compound of the invention to a patient requiring treatment, or alternatively to the use of a compound of the invention in the manufacture of a medicament for treating cancer, osteoporosis, Type 2 diabetes, or an immune disease, or alternatively to a pharmaceutical composition for treating cancer, osteoporosis, Type 2 diabetes, or an immune disease, comprising a compound of the invention.

The cancer to be treated by a compound of the invention may be selected from, but is not limited to, leukaemia, ovarian cancer and breast cancer.

The immune disease to be treated by a compound of the invention may be selected from, but is not limited to, asthma, eczema, allergic rhinitis, Type 1 diabetes, rheumatoid arthritis, and lupus.

General Synthesis Methodology

The compounds of the invention may be prepared according to any known techniques. The following is a general description of the synthesis of compound I. Similar pathways may be employed for preparing other compounds of the invention.

Referring to Scheme 1, the known glycal 1[13] may be converted into the bromoalkene 2 via a cyclopropane intermediate that reacts spontaneously with sodium acetate. Stereoselective alkyne substitution of the acetate with bis(trimethylsilyl)acetylene under Lewis acidic conditions with tin tetrachloride produces a mixture of the acetonide 3 and diol 4. After separation, acetonide 3 can be converted into 4 by treatment with trifluoroacetic acid to provide further diol 4. Removal of the silyl group followed by sodium periodate cleavage affords an aldehyde that undergoes a Wittig reaction to give the unsaturated ester as a separable mixture of the (Z) isomer 5 and the (E) isomer 6 (4:1 ratio of 5:6).

Scheme 1

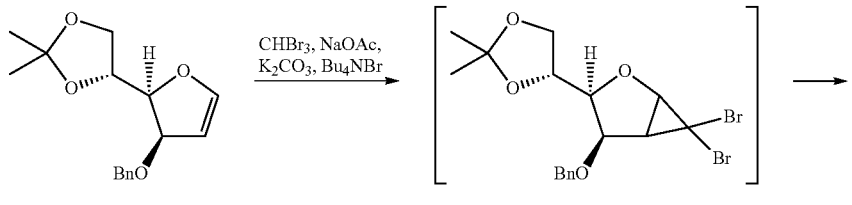

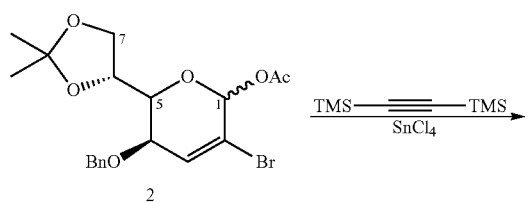

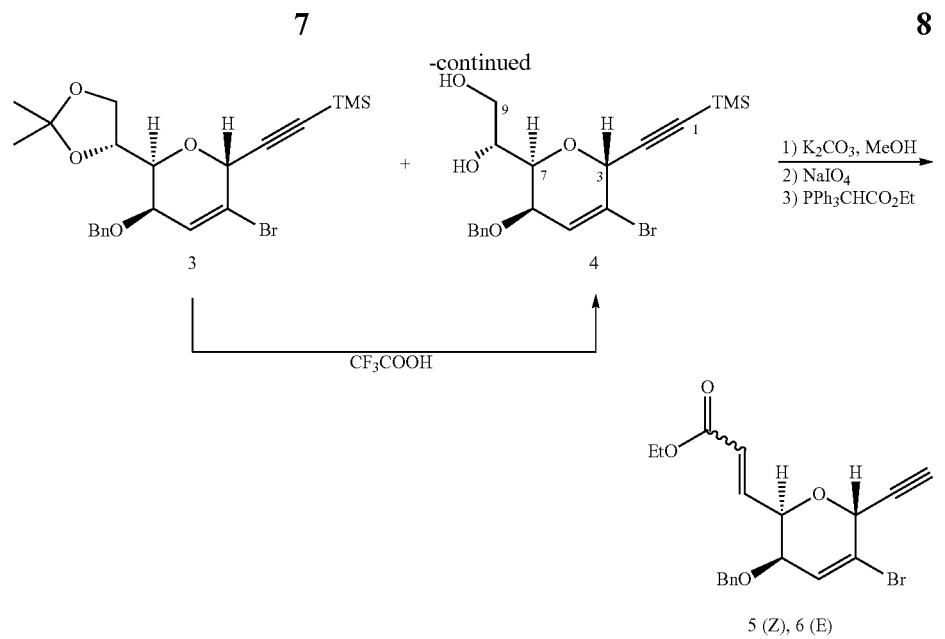

Each isomer is then individually subjected to the following set of reactions, as shown in Schemes 2 and 3. Oxymercuration of 5 or 6 affords the methyl ketone 7 or 11 and reduction proceeds stereoselectively to provide the alcohol 8 or 12. Palladium-catalysed carbonylation and lactone formation gives the furo[3,4-b]pyranone 9 or 13. Debenzylation leads to the final compound 10 or 14.

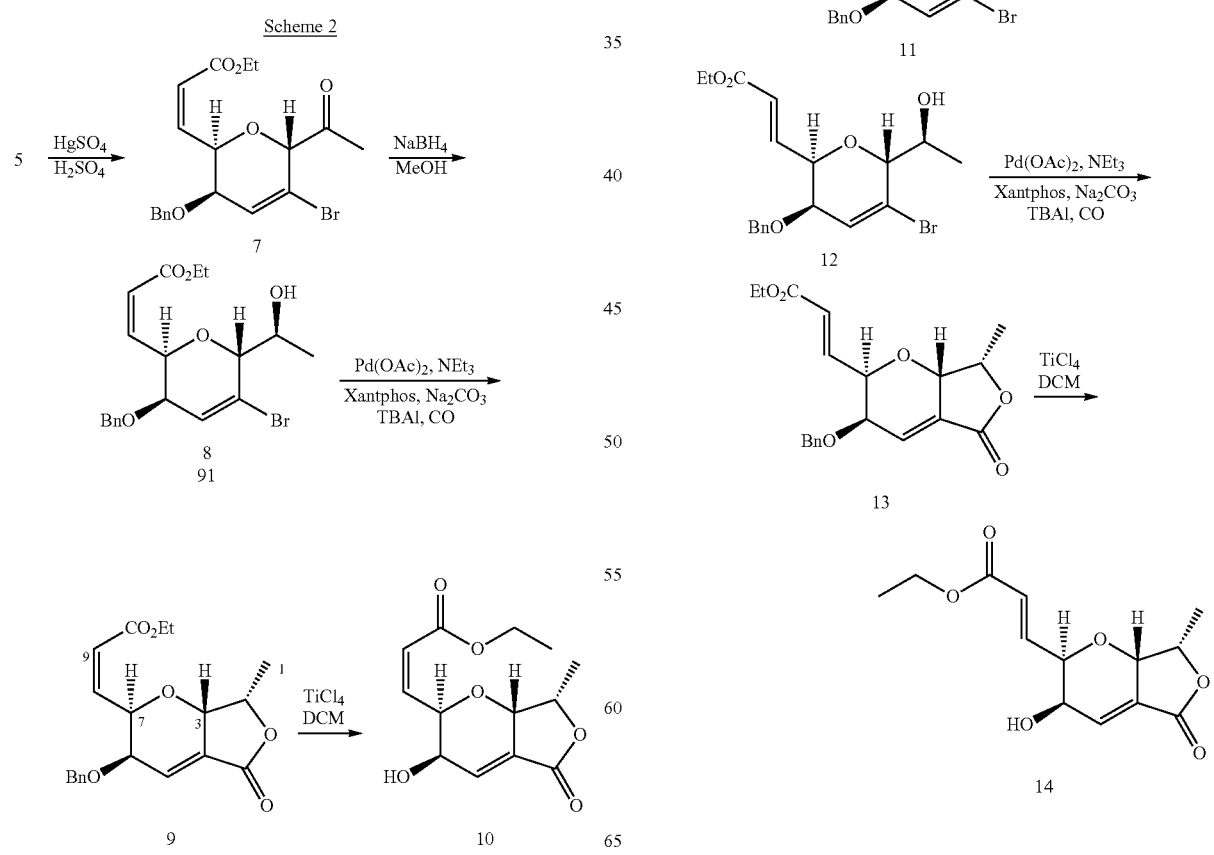

As shown in Scheme 4, the enal 15 can also be derived from diol 4. Oxymercuration affords the ketoaldehyde 16, which is reduced under Luche conditions to provide the diol 17. Carbonylation and deprotection gives the diol 19.
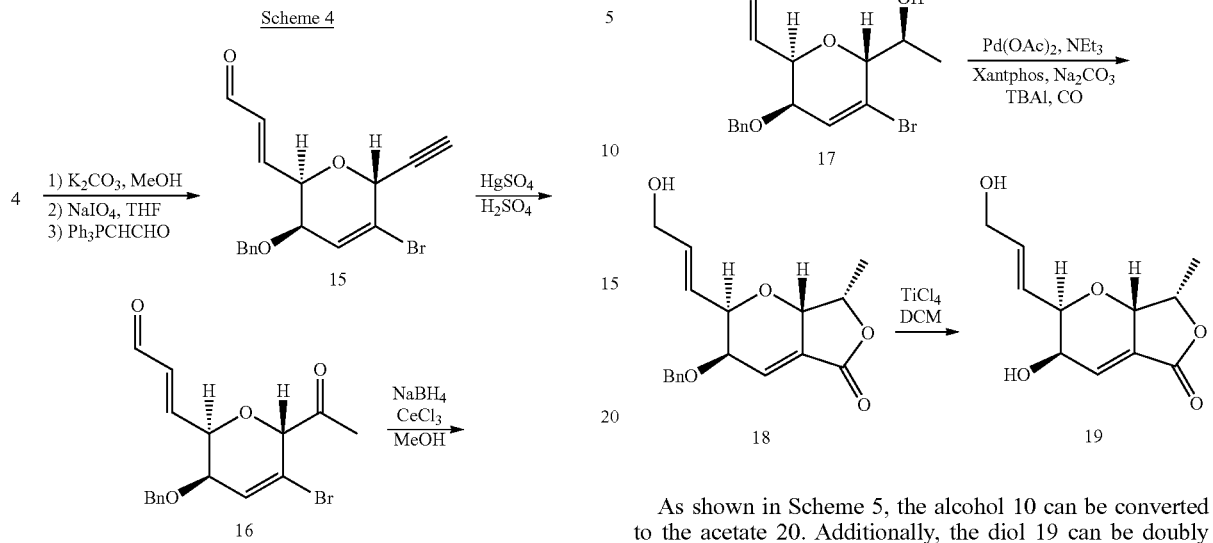
Scheme 4
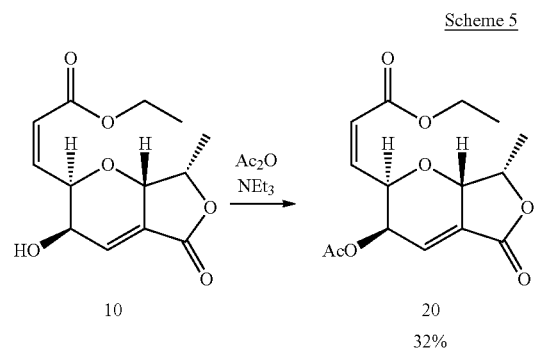
As shown in Scheme 5, the alcohol 10 can be converted to the acetate 20. Additionally, the diol 19 can be doubly acetylated to form diacetate 21 or monomethylated to give methyl ether 22.
Scheme 5
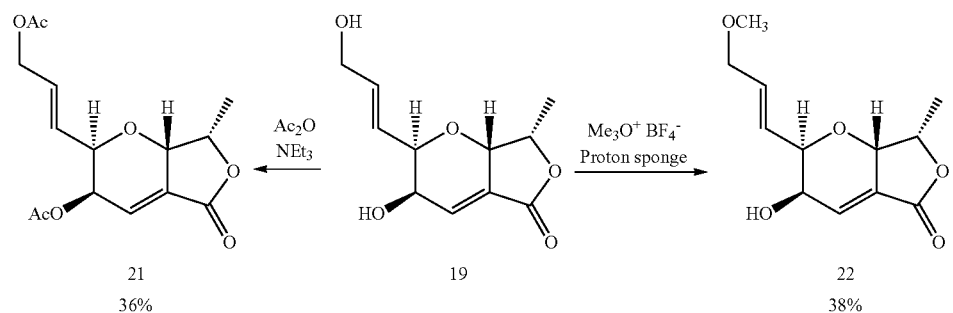

Biological Activity

The compounds of the invention exhibit cytotoxicity and growth inhibition of a range of human, animal and bacterial cell lines, and inhibition of kinases relevant to cancer, diabetes, immune disease or osteoporosis.

Cancer assays were performed using MTT cell proliferation assays with three different immortalised cell lines: a human leukaemia cell line (HL-60), an ovarian cancer cell line (1A9) and a breast cancer cell line (MCF7).

Kinase inhibition assays were conducted by Life Technologies using their SelectScreen® Whole Panel ACCESS Biochemical Kinase Profiling Service. The Z'-LYTE® Screening Protocol was used to obtain the results for the following kinases: AMPK A2/B1/G1, BMX, BTK, MAPK14 (p38 alpha), PLK1, TXK. The LanthaScreen Protocol was used to obtain the result for the following kinase: NUAK2.

AMPK A2/B1/G1 refers to an AMP-activated protein kinase (AMPK) which is a heterotrimeric complex that acts as a sensor of cellular energy levels. The signalling cascades initiated by activating AMPK are critical to regulating metabolic events in the liver, skeletal muscle, heart, adipose tissue, and pancreas. An impairment in fuel metabolism that occurs in obesity is a factor leading to Type 2 diabetes. The insulin resistance associated with Type 2 diabetes is most profound at the level of skeletal muscle, the primary site of glucose and fatty acid utilisation. Activation of AMPK is of interest for the treatment of Type 2 diabetes.

Bone marrow tyrosine kinase (BMX) is a non-receptor tyrosine kinase that belongs to the Src-related TEC subfamily of tyrosine kinases. It is an important regulator of various cellular processes including apoptosis, cell survival, cellular differentiation, cell migration, and transformation. A positive result from a BMX kinase assay is an indicator of potential therapeutic treatment of cancer.

The Src-family kinases are examples of proteins that utilise autophosphorylation to sustain their activated states. Src kinases are involved in intracellular signalling pathways that influence cell growth and cell adhesion strength. The latter contributes to the control of cell migration. In this way, Src-kinase deregulation can enhance tumour growth and invasive potential of cancer cells. Proto-oncogene tyrosine-protein kinase Src also known as proto-oncogene c-Src or simply c-Src is a non-receptor protein tyrosine kinase protein that in humans is encoded by the SRC gene. This protein phosphorylates specific tyrosine residues in other proteins. An elevated level of activity of c-Src tyrosine kinase is suggested to be linked to cancer progression by promoting other signals. Therefore, inhibition of c-Src kinase provides a potential cancer therapy.

MAPK14 refers to a mitogen-activated protein kinase 14 (p38 alpha) which is a member of the stress-activated protein kinase class of MAPKs, MAPK14 is activated by environmental stresses and cytokines, and requires phosphorylation (often by MAPK kinase). MAPK14 is involved in cell differentiation, proliferation, development and transcription regulation. Inhibition of this kinase is relevant to the treatment of cancer.

NUAK2 is a melanoma oncogene. PLK1 is a proto-oncogene involved in colon and lung cancers. Inhibition of these kinases provide a potential cancer therapy.

Bruton tyrosine kinase (BTK) is a cytoplasmic tyrosine kinase belonging to the SRC-related TEC subfamily of tyrosine kinases. It is involved in primary immunodeficiency disease. Mutations in the BTK gene have been linked to severe developmental blocks in human B-cell ontogeny and immunodeficiency disorders.

TXK1 is another member of the TEC kinase family. Along with close relatives BMS, ITK and BTK, this kinase signals downstream of antigen receptors and other types of receptors. It is involved in T-helper 1 (Th1) cytokine production.

Compound 10 was found to be growth inhibitory towards immortalised HL-60 (human leukaemia) and MCF7 (breast cancer) cell lines ($IC_{50}$ 3.6 and 9.0 µM, respectively) using MTT assays. This compound also demonstrated inhibition of the following kinases (single-point, percent inhibitions at 10 µM is given in brackets): BTK (Bruton's tyrosine kinase, 83%), AMPK A2/B1/G1 (81%), PLK1 (81%), BMX (80%), NUAK2 (76%), MAPK14 (p38 alpha, 74%), TXK (71%).

Compound 14 was found to be growth inhibitory towards immortalised HL-60 (human leukaemia) and 1A9 (ovarian cancer) cell lines ($IC_{50}$ 2.2 and 3.4 µM, respectively) using MTT assays.

Compound 19 was found to be modestly growth inhibitory towards immortalised HL-60 (human leukaemia) cell line ($IC_{50}$ 42 µM) using a MTT assay.

Therefore, compounds 10, 14 and 19 represent potential leads for the treatment of cancer, Type 2 diabetes and immune disease. The inhibition of PTH-induced bone resorption by the parent compound TAN-2483B also indicates a potential therapeutic application in osteoporosis by this class of compounds.

Pharmaceutical Formulations and Administration

The compounds of the invention may be administered to a patient by a variety of routes, including orally, parenterally, by inhalation spray, topically, rectally, nasally, buccally, intravenously, intra-muscularly, intra-dermally, subcutaneously or via an implanted reservoir, preferably intravenously. The amount of compound to be administered will vary widely according to the nature of the patient and the nature and extent of the disorder to be treated. Typically the dosage for an adult human will be in the range 50-4800 µg/m$^2$ or µg/kg. The specific dosage required for any particular patient will depend upon a variety of factors, including the patient's age, body weight, general health, sex, etc.

For oral administration the compounds of the invention can be formulated into solid or liquid preparations, for example tablets, capsules, powders, solutions, suspensions and dispersions. Such preparations are well known in the art as are other oral dosage regimes not listed here. In the tablet form the compounds may be tableted with conventional tablet bases such as lactose, sucrose and corn starch, together with a binder, a disintegration agent and a lubricant. The binder may be, for example, corn starch or gelatin, the disintegrating agent may be potato starch or alginic acid, and the lubricant may be magnesium stearate. For oral administration in the form of capsules, diluents such as lactose and dried corn-starch may be employed. Other components such as colourings, sweeteners or flavourings may be added.

When aqueous suspensions are required for oral use, the active ingredient may be combined with carriers such as water and ethanol, and emulsifying agents, suspending agents and/or surfactants may be used. Colourings, sweeteners or flavourings may also be added.

The compounds may also be administered by injection in a physiologically acceptable diluent such as water or saline. The diluent may comprise one or more other ingredients such as ethanol, propylene glycol, an oil or a pharmaceutically acceptable surfactant. In one preferred embodiment, the compounds are administered by intravenous injection, where the diluent comprises an aqueous solution of sucrose, L-histidine and a pharmaceutically acceptable surfactant, e.g. Tween 20.

The compounds may also be administered topically. Carriers for topical administration of the compounds include mineral oil, liquid petrolatum, white petrolatum, propylene glycol, polyoxyethylene, polyoxypropylene compound, emulsifying wax and water. The compounds may be present as ingredients in lotions or creams, for topical administration to skin or mucous membranes. Such creams may contain the active compounds suspended or dissolved in one or more pharmaceutically acceptable carriers. Suitable carriers include mineral oil, sorbitan monostearate, polysorbate 60, cetyl ester wax, cetearyl alcohol, 2-octyldodecanol, benzyl alcohol and water.

The compounds may further be administered by means of sustained release systems. For example, they may be incorporated into a slowly dissolving tablet or capsule.

Any reference to prior art documents in this specification is not to be considered an admission that such prior art is widely known or forms part of the common general knowledge in the field.

As used in this specification, the words "comprises", "comprising", and similar words, are not to be interpreted in an exclusive or exhaustive sense. In other words, they are intended to mean "including, but not limited to".

The invention is further described with reference to the following examples. It will be appreciated that the invention as claimed is not intended to be limited in any way by these examples.

EXAMPLES

Example 1: (−)-TAN-2483B Z-ethyl ester (10)

Synthesis of Compound 2

A solution of glycal 1 (493 mg, 1.78 mmol) in a solution of bromoform (5 mL) was treated with $K_2CO_3$ (1.50 g, 10.9 mmol), sodium acetate (540 mg, 6.48 mmol) and 18-crown-6 (20 mg, 0.076 mmol). To the resulting suspension was added tetra-n-butylammonium bromide (93 mg, 0.304 mmol) and the mixture stirred at room temperature for 24 hours. It was then heated to 82° C. and stirred for two days. The reaction mixture was filtered and concentrated to provide a dark-brown liquid. This crude material was purified by column chromatography (9:1 petroleum ether:ethyl acetate) to obtain the product acetate 2 as an inseparable mixture of anomers and as a colourless oil (364 mg, 47%, 4:1α:β) together with starting material as a yellow oil (69 mg, 14%, contaminated with bromoform). 2: $R_f$ 0.18 (10:1 petroleum ether:ethyl acetate); $^1$H NMR: ($CDCl_3$) δ=7.38-7.32 (complex m, 5H, Bn), 6.49 (d, J=5.3, 0.2H, H-3), 6.48 (d, J=6.1 Hz, 0.8H, H-3), 6.35 (s, 0.2H, H-1), 6.25 (s, 0.8H, H-1), 4.71 (s, 1.6H, $PhCH_2$), 4.69 (s, 0.4H, $PhCH_2$), 4.40 (m, 1H, H-6), 4.10 (m, 1H, H-7a), 4.04 (dd, J=8.8, 4.7 Hz, 0.8H, H-7b), 3.94 (apparent d, J=6.1 Hz, 0.8H,H-4), 3.92 (dd, J=5.8, 2.6 Hz, 0.2H, H-4), 3.89-3.84 (complex m, 0.4H, H-5, H-7b), 3.70 (dd, J=8.5, 2.0 Hz, 0.8H, H-5), 2.15 (s, 2.4H, Ac), 2.12 (s, 0.6H, Ac), 1.41 (s, 0.6H, $(CH_3)_2C$), 1.39 (s, 2.4H, $(CH_3)_2C$) 1.38 (s, 0.6H, $(CH_3)_2C$) 1.36 (s, 2.4H, $(CH_3)_2C$); $^{13}$C NMR: ($CDCl_3$) δ 169.5 (C, $CH_3CO$), 169.2 (C, $CH_3CO$), 138.0 (C, Bn), 137.8 (C, Bn), 131.6 (CH, C-3), 130.2 (CH, C-3), 128.39 (CH, Bn), 128.24 (CH, Bn), 128.06 (CH, Bn), 127.99 (CH, Bn), 127.90 (CH, Bn), 127.54 (CH, Bn), 124.6 (CH,C-2), 122.6 (CH,C-2), 109.5 (C, $(CH_3)_2C$), 90.6 (CH, C-1), 90.0 (CH, C-1), 73.3 (broad, 2×CH, 2×C-6), 73.0 (CH, C-5), 72.1 (broad, $CH_2$ and CH, $PhCH_2$ and C-5), 71.9 ($CH_2$, $PhCH_2$), 69.5 (CH, C-4), 69.1 (CH, C-4), 67.1 ($CH_2$, C-7), 67.0 ($CH_2$, C-7), 27.01 ($CH_3$, $(CH_3)_2C$), 26.91 ($CH_3$, $(C_3)_2C$), 25.93 ($CH_3$, $(CH_3)_2C$), 25.31 ($CH_3$, ( $CH_3)_2C$), 20.92 ($CH_3$, Ac), 20.91 ($CH_3$, Ac); IR (film from $CHCl_3$) $v_{max}$ 1812, 1644, 1604, 1496, 1454, 1328, 1308, 1288, 786, 761, 648 $cm^{-1}$; HRMS: m/z $C_{19}H_{27}^{79}BrO_6N^+$ $[M+NH_4]^+$ calcd 444.1016, found 444.1023, m/z $C_{19}H_{27}^{81}BrO_6N^+$ $[M+NH_4]^+$ calcd 446.0998, found 446.1007.

Synthesis of Compounds 3 and 4

Bis(trimethyl)silylacetylene (1.0 mL, 5.11 mmol) and acetate 2 (546 mg, 1.27 mmol) were dissolved in dry $CH_2Cl_2$ (12 mL) and cooled to −78° C. Then $SnCl_4$ (1.27 mL, 1M solution in $CH_2Cl_2$) was added dropwise into the cold solution. The combined solution was stirred for 2 hours at the same temperature and then was quenched with $NaHCO_3$ (15 mL) and extracted into $CH_2Cl_2$ (2×10 mL). The crude mixture containing acetonide 3 and diol 4 was purified by gradient column chromatography (20:1 to 2:1 petroleum ether:ethyl acetate) to yield 3 (92 mg, 15%) as a colourless oil and diol 4 (156 mg, 29%) as a colourless oil.

The remaining 3 could be converted into 4 in the following manner. Acetonide-protected alkyne 3 (95 mg, 0.19 mmol) was dissolved in 2 mL of acetonitrile and cooled to 0° C. using an ice-water bath. Then it was treated with trifluoroacetic acid (0.5 mL, 6.5 mmol) and slowly warmed up to room temperature. After stirring for 45 min at room temperature, the solution was carefully quenched with powdered $NaHCO_3$ and diluted with distilled water. The organic compounds were extracted into $CH_2Cl_2$, the organic phase was dried, filtered and concentrated to afford diol 4 (81 mg, quantitative) as a colourless oil (combined yield of 4: 44%).

3: $R_f$ 0.45 (5:1 petroleum ether:ethyl acetate); $[α]_D^{22}$=−45 (c 0.32, $CH_2Cl_2$) $^1$H NMR: ($CDCl_3$) δ=7.37-7.27 (complex m, 5H, Bn), 6.26 (d, J=5.5 Hz, 1H, H-5), 4.92 (s, 1H, H-3), 4.69 (s, 2H, $PhCH_2$), 4.40 (apparent dd, J=13.7, 5.4 Hz $^1$H, H-9a), 4.15 (dd, J=14.0, 6.6 Hz, 1H, H-9b), 3.97 (complex m, 1H, H-8), 3.90 (complex m, J, 2H, H-7, H-6), 1.41 (s, 3H, (C$\underline{H}_3)_2$C), 1.40 (s, 3H, ($\underline{CH}_3)_2$C), 0.18 (s, 9H, ($\underline{CH}_3)_3$Si); $^{13}$C NMR: ($CDCl_3$) δ 138.0 (C, Bn), 128.36 (CH, Bn), 128.08 (CH, Bn), 127.84 (CH, Bn), 126.9 (CH,C-5), 124.9 (C, C-4), 109.4 (C, $(CH_3)_2\underline{C}$), 99.4 (C, C-2), 92.3 (C, C-1), 74.2 (CH, C-6), 72.9 (CH, C-8), 72.1 ($CH_2$, $PhCH_2$), 69.9 (CH, C-3), 69.9 (CH, C-7), 67.6 ($CH_2$, C-9), 26.8 ($CH_3$, ($\underline{CH}_3)_2$C), 25.5 ($CH_3$, ($\underline{CH}_3)_2$C); IR (film from $CH_2Cl_2$) $v_{max}$ 2986, 2959, 2873, 1643, 1455, 1297, 1106, 1079, 1212, 906, 841, 731, 697 $cm^{-1}$; HRMS: m/z $C_{22}H_{30}^{81}BrO_4Si^+$ $[M+H]^+$ calcd 467.1074, found 467.1056. 4: $R_f$ 0.38 (2:1 petroleum ether:ethyl acetate); $[α]_D^{21}$=−100 (c 0.2, $CH_2Cl_2$); $^1$H NMR: ($CDCl_3$) δ=7.38-7.31 (complex m, 5H, Bn), 6.37 (d, J=5.4 Hz, 1H, H-5), 4.95 (s, 1H, H-3), 4.73 (d, J=11.7 Hz, 1H, $PhCH_2$), 4.59 (d, J=11.7 Hz, 1H, $PhCH_2$), 4.02-3.96 (complex m, 3H, H-6, H-7, H-8), 4.01-3.84 (apparent d, J=11.6 Hz, H, H-9a), 3.78 (dd, J=11.6, 4.6 Hz, 1H, H-9b), 0.18 (s, 9H, $(CH_3)_3Si$); $^{13}$C NMR: ($CDCl_3$) δ 137.6 (C, Bn), 128.69 (CH, Bn), 128.55 (CH, Bn), 128.19 (CH, Bn), 126.4 (CH, C-5), 125.5 (CH, C-4), 99.3 (C, C-2), 92.4 (C, C-1), 72.5 (CH, C-6), 71.2 ($CH_2$, $PhCH_2$), 69.93 (CH, C-7 or C-8 or C-3), 69.76 (CH, C-7 or C-8 or C-3), 69.38 (CH, C-7 or C−8 or C-3) 64.0 ($CH_2$, C-9); IR (film from $CH_2Cl_2$) $v_{max}$ 3486, 2985, 2873, 1644, 1454, 1297, 1106, 1079, 912, 843, 732, 698 $cm^{-1}$; HRMS: m/z $C_{19}H_{25}^{81}BrO_4SiNa^+$ $[M+Na]^+$ calcd 449.0580, found 449.0575.

Synthesis of Compounds 5 and 6

Diol 4 (270 mg, 0.63 mmol) was dissolved in dichloromethane (7.5 mL) and treated with MeOH (1.5 mL). The reaction mixture became a white suspension and was stirred until the reaction was deemed complete (2 hours). This mixture was diluted with $CH_2Cl_2$ and filtered into a brine solution. The aqueous layer was extracted with $CH_2Cl_2$ (2×10 mL) and the combined organic fractions evaporated at room temperature under reduced pressure to afford the diol-containing terminal alkyne as a white solid. The product was used in the next reaction without further purification. $R_f$ 0.29 (1:1 petroleum ether:ethyl acetate); m.p. 147.9-148.8° C.; $[\alpha]_D^{22}$=−100 (c 0.1, $CH_2Cl_2$); $^1H$ NMR: ($CDCl_3$) δ=7.39-7.31 (complex m, 5H, Bn), 6.42 (d, J=5.4 Hz, 1H, H-5), 5.00 (s, 1H, H-3), 4.74 (d, J=11.8 Hz, 1H, $PhCH_2$), 4.60 (d, J=11.7 Hz, 1H, $PhCH_2$), 4.03 (dd, J=5.6, 2.2 Hz, 1H, H-6), 3.99-3.79 (complex m, 2H, H-7, H-8), 3.86-3.84 (apparent d, J=10.6 Hz, 1H, H-9a), 3.78 (dd, J=10.9, 5.2 Hz, 1H, H-9b), 2.53 (d, J=2.2 Hz, 1H, H-1); $^{13}C$ NMR: ($CDCl_3$) δ 137.6 (C, Bn), 128.69 (CH, Bn), 128.22 (CH, Bn), 128.04 (CH, Bn), 126.7 (CH, C-5), 125.1 (CH, C-4), 78.2 (C, C-2), 75.0 (C, C-1), 72.5 (CH, C-7 or C-8), 71.3 ($CH_2$, $PhCH_2$), 69.8 (CH, C-7 or C-8), 69.4 (CH, C-6), 69.2 (CH, C-3) 63.8 ($CH_2$, C-9); IR (film from $CH_2Cl_2$) $v_{max}$ 3486, 3088, 2981, 1496, 1455, 1369, 1339, 1252, 1214, 1129, 987, 848 $cm^{-1}$; HRMS: m/z $C_{16}H_{18}{}^{81}BrO_4{}^+$ [M+H]$^+$ calcd 353.0388, found 353.0367.

A solution of the crude diol described above (120 mg, 0.34 mmol) in THF (10 mL) and pH 7 phosphate buffer (3 mL) was treated with $NaIO_4$ (508 mg, 2.38 mmol) in one portion. The resulting mixture was stirred for 1 hour, diluted with brine (50 mL), and extracted with $Et_2O$ (3×50 mL). The combined organic layers were washed with brine, dried over $MgSO_4$ and evaporated to give a colourless oil, which was used without further purification. Next the crude aldehyde product was dissolved in THF (10 mL) and treated with ethyl triphenylphosphoranylidene acetate (236 mg, 0.68 mmol). The solution was stirred overnight before concentrating under reduced pressure and purifying with column chromatography (14:1 petroleum ether:ethyl acetate) to yield both (Z)-isomer 5 (94 mg, 38%) and (E)-isomer 6 (25 mg, 10%) as colourless oils (combined yield: 48% over three steps). 5: $R_f$ 0.33 (14:1 petroleum ether:ethyl acetate); $[\alpha]_D^{20}$=−188 (c 0.26, $CH_2Cl_2$); $^1H$ NMR: ($CDCl_3$) δ=7.33-7.26 (complex m, 5H, Bn), 6.35 (dd, J=5.4, 1.2 Hz, 1H, H-5), 6.33 (dd, J=11.3, 6.8 Hz, 1H, H-8), 5.93 (d, J=11.3 Hz, 1H, H-9), 5.55 (broad d, J=6.6 Hz, 1H, H-7), 5.02 (s, 1H, H-3), 4.58 (d, J=11.4 Hz, 1H, $PhCH_2$), 4.50 (d, J=11.7 Hz, 1H, $PhCH_2$), 4.20 (dd, J=5.6, 2.7 Hz 1H, H-6), 4.14 (q, J=7.2 Hz, 2H, OEt), 2.50 (s, 1H, H−1), 1.28 (t, J=7.2 Hz, 3H, OEt); $^{13}C$ NMR: ($CDCl_3$) δ 165.6 (C, C-10), 144.8 (CH, C-8), 137.5 (C, Bn), 128.40 (CH, Bn), 128.2 (CH, C-5), 127.98 (CH, Bn), 127.89 (CH, Bn), 120.5 (C, C-9), 78.1 (C, C-2), 75.1 (C, C-1), 71.8 ($CH_2$, Bn), 71.3 (CH, C-6), 71.0 (CH, C-7), 68.8 (CH, C-3), 60.4 ($CH_2$, OEt), 14.2 ($CH_3$, OEt); IR (film from $CH_2Cl_2$) $v_{max}$ 3031, 2931, 2872, 2116, 1648, 1539, 1454, 1497, 1388, 1366, 1334, 1031, 911, 846, 735, 698 $cm^{-1}$; HRMS: m/z $C_{19}H_{21}{}^{81}BrO_4{}^+$ [M+H]$^+$ calcd 393.0521, found 393.0533. 6: $R_f$ 0.45 (2:1 petroleum ether: ethyl acetate); $[\alpha]_D^{20}$=−112 (c 0.34, $CH_2Cl_2$); $^1H$ NMR: ($CDCl_3$) δ 7.37-7.26 (complex m, 5H, Bn), 7.02 (dd, J=15.8, 4.2 Hz, 1H, H-8), 6.34 (d, J=5.5 Hz, 1H, H-5), 6.22 (dd, J=15.8, 1.5 Hz, 1H, H-9), 5.09 (s, 1H, H-3), 4.73 (m, 1H, H-7), 4.61 (d, J=11.8 Hz, 1H, $PhCH_2$), 4.53 (d, J=11.8 Hz, 1H, $PhCH_2$), 4.23 (q, J=7.1 Hz, 2H, OEt), 3.92 (dd, J=5.3, 2.8 Hz, 1H, H-6), 2.53 (d, J=2.1 Hz, 1H, H-1), 1.31 (t, J=7.1 Hz, 3H, OEt); $^{13}C$ NMR: ($CDCl_3$) δ 166.0 (C, C-10), 142.5 (CH, C-8), 137.4 (C, Bn), 128.13 (CH, Bn), 128.03 (CH, Bn), 127.99 (CH, Bn), 126.6 (CH, C-5), 124.9 (C, C-4), 122.7 (CH, C-9), 77.9 (C, C-2), 75.3 (CH, C-1), 72.2 (CH, C-7), 71.1 ($CH_2$, $PhCH_2$), 71.0 (CH, C-6), 60.5 ($CH_2$, OEt), 14.6 ($CH_3$, OEt); IR (film from $CH_2Cl_2$) $v_{max}$ 2360, 2115, 1664, 1496, 1454, 1392, 1368, 898, 847, 798, 645, 631, 603 $cm^{-1}$; HRMS: m/z $C_{19}H_{23}{}^{81}BrO_4N^+$ [M+$NH_4$]$^+$ calcd 408.0805, found 408.0819.

Synthesis of Compound 7

A sample of Z-ethyl ester 5 (125 mg, 0.32 mmol) was dissolved in THF (1.5 mL). $HgSO_4$ in $H_2SO_4$ (10% aqueous solution, 1.5 mL, 19 mg, 0.2 equiv) was added to this solution. The reaction mixture was stirred at room temperature for 16 hours. The mixture was diluted with $Et_2O$ (5 mL) and carefully neutralised with $NaHCO_3$ powder until pH=7 was reached. The aqueous layer was washed with $Et_2O$ (3×5 mL). The organic layers were combined and dried over $MgSO_4$. The crude product was chromatographed (9:1 petroleum ether: ethyl acetate) to yield the product 7 as a clear oil (95 mg, 72%). 7: $R_f$ 0.31 (9:1 petroleum ether:ethyl acetate); $[\alpha]_D^{21}$=−133 (c 0.14, $CH_2Cl_2$); $^1H$ NMR: ($CDCl_3$) δ 7.34-7.28 (complex m, 5H, Bn), 6.48 (d, J=5.2 Hz, 1H,H-5), 6.36 (dd, J=11.6, 7.2 Hz, 1H,H-8), 5.94 (d, J=11.9 Hz, 1H,H-9), 5.31 (broad d, J=6.9 Hz, 1H, H-7), 4.74 (s, 1H, H-3), 4.59 (d, J=11.9 Hz, 1H, $PhCH_2$), 4.52 (d, J=11.7 Hz, 1H, $PhCH_2$), 4.17 (dd, J=5.0, 3.0 Hz, 1H, H-6), 4.13 (q, J=7.1 Hz, 2H, OEt), 2.32 (s, 3H, H-1), 1.27 (t, J=7.1 Hz, 3H, OEt); $^{13}C$ NMR: ($CDCl_3$) δ 202.8 (C, C-2), 165.3 (C, C-10), 144.5 (CH, C-8), 137.5 (C, Bn), 128.43 (CH, C-5), 128.40 (CH, Bn), 128.04 (CH, Bn), 127.97 (CH, Bn), 121.50 (C, C-9), 81.2 (CH,C-3), 71.8 ($CH_2$, Bn), 71.4 (CH, C-6), 71.2 (CH, C-7), 60.5 ($CH_2$, OEt), 28.1 ($CH_3$, C-1), 14.1 ($CH_3$, OEt); IR (film from $CH_2Cl_2$) $v_{max}$ 3063, 2872, 1649, 1496, 1454, 1388, 1302, 979, 697 $cm^{-1}$; HRMS: m/z $C_{19}H_{25}BrO_5N^+$ [M+$NH_4$]$^+$ calcd 426.0911, found 426.0902.

Synthesis of Compound 8

A sample of methyl ketone 7 (95 mg, 0.23 mmol) was dissolved in MeOH (2 mL) and cooled to −78° C. using an acetone-dry ice bath and treated with $NaBH_4$ (9 mg, 0.28 mmol). The solution was stirred for 45 minutes at the same temperature to complete the reaction. Unreacted $NaBH_4$ was quenched with acetone (1 mL). The solvent was removed under reduced pressure and the residue redissolved in dichloromethane. The organic phase was washed with water. The extracted organic layer was evaporated and purified by column chromatography (5:1 petroleum ether:ethyl acetate) to yield product 8 as a colourless oil (85 mg, 91%). 8: $R_f$ 0.24 (5:1 petroleum ether: ethyl acetate); $[\alpha]_D^{20}$=−65 (c 0.2, $CH_2Cl_2$). $^1H$ NMR: ($CDCl_3$) δ=7.34-7.28 (complex m, 5H, Bn), 6.48 (dd, J=4.8, 1.4 Hz, 1H, H-5), 6.44 (dd, J=11.7, 7.8 Hz, 1H, H-8), 5.99 (d, J=11.8 Hz, 1H, H-9), 5.80 (ddd, J=7.6, 3.2, 1.6 Hz, 1H, H-7), 4.62 (d, J=12.0 Hz, 1H, $PhCH_2$), 4.55 (d, J=12.0 Hz, 1H, $PhCH_2$), 4.36 (m, 1H, H-2), 4.16 (q, J=7.1 Hz, 2H, OEt), 4.12 (partially obscured dd, J=4.2, 3.4 Hz, 1H, H-6), 4.05 (apparent s, 1H, H-3), 1.34 (d, 3H, J=6.9 Hz, H-1), 1.28 (t, J=7.2 Hz, 3H, OEt); $^{13}C$ NMR: ($CDCl_3$) δ 165.7 (C, C-10), 144.3 (CH, C-8), 137.8 (C, Bn), 129.2 (CH, C-5), 128.39 (CH, Bn), 128.87 (CH, Bn), 127.84 (CH, Bn), 125.2 (C, C-4), 122.5 (CH,C-9), 79.5 (CH, C-3), 71.8 (CH, C-6), 71.4 ($CH_2$, $PhCH_2$), 69.9 (CH, C-7), 68.0 (CH, C-2), 60.5 ($CH_2$, OEt), 19.6 ($CH_3$, C-1), 14.1 ($CH_3$, OEt); IR (film from $CH_2Cl_2$) $v_{max}$ 3467, 3031, 2980, 2930, 1650, 1454, 1232, 1147, 856, 827, 697 $cm^{-1}$; HRMS: m/z $C_{19}H_{25}O_5{}^+$ [M+H]$^+$ calcd 333.1697, found 333.1686.

Synthesis of Compound 9

Alcohol 8 (42 mg, 0.11 mmol) was dissolved in 1,4-dioxane (2 mL). Then XantPhos (15 mg, 0.025 mmol, 20 mol %), palladium acetate (6 mg, 0.025 mmol, 20 mol %), sodium carbonate (67 mg, 0.63 mmol), TBAI (9 mg, 0.025 mmol) and triethylamine (0.18 ml, 1.26 mmol) were added sequentially. CO gas was bubbled through the reaction mixture for a few minutes to saturate the solution with CO.

Then the flask was connected to a reflux condenser under an atmosphere of CO (balloon). The whole set-up was evacuated and purged with CO three times and stirred vigorously at 95° C. overnight. Another portion of XantPhos and palladium acetate (10 mol % each) was added after 16 hours and the mixture stirred vigorously at 95° C. under CO until the reaction was complete (a further 3 hours). The mixture was diluted with dichloromethane and filtered through a silica plug. The crude product was purified by column chromatography (3:1 petroleum ether: ethyl acetate) to yield the lactone 9 as a colourless oil (22 mg, 60%). 9: $R_f$ 0.37 (5:1 petroleum ether:ethyl acetate); $[\alpha]_D^{20}$=−178 (c 0.18, $CH_2Cl_2$); $^1$H NMR: ($CDCl_3$) δ=7.35-7.28 (complex m, 5H, Bn), 7.22 (dd, J=5.4, 3.2 Hz, 1H, H-5), 6.49 (dd, J=11.5, 7.7 Hz, 1H, H-8), 5.99 (dd, J=11.5, 1.0 Hz, 1H, H-9), 5.28 (m, 1H, H-7), 5.14 (dd, J=7.5, 3.2 Hz, 1H, H-3), 4.85 (apparent q, J=6.8 Hz, 2H, H-2), 4.60 (d, J=11.9 Hz, 1H, $PhCH_2$), 4.51 (d, J=12.2 Hz, 1H, $PhCH_2$), 4.42 (dd, J=5.4, 2.9 Hz 1H, H-6), 4.15 (q, J=7.2 Hz, 2H, OEt), 1.29-1.26 (apparent m, 6H, OEt, C-1); $^{13}$C NMR: ($CDCl_3$) δ 166.4 (C, C-13), 165.6 (C, C-10), 145.5 (CH, C-8), 137.4.0 (C, Bn), 134.9 (CH, C-5), 132.3 (C, C-4), 128.48 (CH, Bn), 128.07 (CH, Bn), 127.80 (CH, Bn), 122.3 (CH,C-9), 78.4 (CH, C-2), 71.8 ($CH_2$, $PhCH_2$), 71.6 (CH, C-7), 71.2 (CH, C-3), 69.5 (CH, C-6), 60.5 ($CH_2$, OEt), 15.4 ($CH_3$, OEt or 1), 14.2 ($CH_3$, OEt or C-1); IR (film from $CH_2Cl_2$) $v_{max}$ 2983, 1650, 1454, 1413, 1386, 1298, 1096, 920, 829, 736, 689, 632 cm$^{-1}$; HRMS: m/z $C_{23}H_{23}O_6^+$ [M+H]$^+$ calcd 362.1595, found 362.1575.

Synthesis of Compound 10

To a solution of lactone 9 (30.0 mg, 0.08 mmol) in $CH_2Cl_2$ (1 mL) was added $TiCl_4$ (27 µL, 0.25 mmol) in $CH_2Cl_2$ (0.1 mL) at 0° C. After stirring at the same temperature for 10 min, the reaction was quenched with saturated aqueous $NaHCO_3$ (5 mL), and the organic layer was separated and extracted with $CH_2Cl_2$ (2×5 mL). The organic layers were combined and dried over anhydrous $MgSO_4$. After filtration and concentration under reduced pressure, the crude product was purified by column chromatography (2:1 petroleum ether:ethyl acetate) to yield (Z)-TAN-2483B ethyl ester 10 as a colourless oil (13 mg, 56%). 10: $R_f$ 0.17 (2:1 petroleum ether:ethyl acetate); $^1$H NMR: ($CDCl_3$) δ=7.16 (dd, J=5.4, 3.4 Hz, 1H, H-5), 6.44 (dd, J=11.7, 7.8 Hz, 1H, H-8), 6.07 (dd, J=11.7, 1.2 Hz, 1H, H-9, 5.32 (ddd, J=7.8, 3.4, 1.4 Hz, 1H, H-7), 5.12 (ddd, J=5.4, 3.2, 1.3 Hz, 1H, H-3), 4.85 (quintet, J=6.8 Hz, 2H, H-2), 4.71 (dd, J=4.8, 3.6 Hz 1H, H-6), 4.19 (q, J=7.2 Hz, 2H, OEt), 1.32-1.28 (apparent m, 6H, OEt, H-1); $^{13}$C NMR: ($CDCl_3$) δ 166.4 (C, C-10), 166.1 (C, C-13), 143.7 (CH, C-8), 135.4 (CH, C-5), 130.9 (C, C-4), 123.3 (CH,C-9), 78.0 (CH, C-2), 72.9 (CH, C-3), 70.4 (CH, C-7), 69.6 (CH, C-6), 60.9 ($CH_2$, OEt), 15.2 ($CH_3$, OEt or C-1), 14.1 ($CH_3$, OEt or C-1), IR (film from $CH_2Cl_2$) $v_{max}$ 3572, 3458, 1650, 1447, 1414, 1386, 1331, 1301, 1121, 1042, 968, 917, 852, 822, 764, 731 cm$^{-1}$; HRMS: m/z $C_{13}H_{17}O_6^+$ [M+H]$^+$ calcd 268.0947, found 269.1012.

Example 2: (−)-TAN-2483B E-ethyl ester (14)

Synthesis of Compound 11

A sample of alkyne 6 (35 mg, 0.09 mmol) was dissolved in THF (0.7 mL). $HgSO_4$ (5 mg, 0.2 equiv, in 0.7 mL of 10% $H_2SO_4$ solution) was added to this solution. Then this solution was stirred at room temperature until the starting material disappeared (overnight). The mixture was diluted with $Et_2O$ (5 mL) and carefully neutralised with powdered $NaHCO_3$ until pH=7. The aqueous layer was washed with $Et_2O$ (3×5 mL). The organic layers were combined and dried over $MgSO_4$. After filtering and concentrating under reduced pressure, the crude product was chromatographed (5:1 petroleum ether: ethyl acetate) to yield the product 11 as clear oil (22 mg, 61%). 11: $R_f$ 0.25 (5:1 petroleum ether: ethyl acetate); $[\alpha]_D^{23}$=−224 (c 0.45, $CH_2Cl_2$); $^1$H-NMR: ($CDCl_3$) $δ_H$ 7.36-7.29 (complex m, 5H, Bn), 6.98 (dd, J=15.8, 4.2 Hz, 1H, H-9), 6.50 (dd, J=4.1, 0.7 Hz, 1H, H-5), 6.19 (dd, J=15.8, 1.4 Hz, 1H, H-8), 4.81 (s, 1H, H-3), 4.62 (d, J=11.7 Hz, 1H, $PhCH_2$), 4.54 (d, J=12.0 Hz, 1H, $PhCH_2$), 4.47 (m, 1H, H-7), 4.24 (q, J=7.2 Hz, 2H, OEt), 3.95 (dd, J=4.3, 3.8 Hz, 1H, H-6), 2.33 (s, 3H, H-1), 1.32 (t, J=7.1 Hz, 3H, OEt); $^{13}$C-NMR: ($CDCl_3$) $δ_C$ 202.6 (C, C-2), 165.3 (C, C-10), 142.1 (CH, C-9), 137.3 (C, Bn), 128.53 (CH, Bn), 128.52 (CH, Bn), 128.09 (CH, Bn), 127.99 (CH, C-5), 123.1 (CH, C-8), 121.2 (C, C-4), 80.8 (CH, C-3), 72.8 (CH, C-7), 71.2 (CH, C-6 and $CH_2$, $PhCH_2$), 60.6 ($CH_2$, OEt), 28.1 ($CH_3$, C-1), 14.2 ($CH_3$, OEt); IR (film from $Et_2O$) $v_{max}$ 3063, 1664, 1642, 1604, 1496, 1419, 924, 866, 612 cm$^{-1}$; HRMS: m/z $C_{19}H_{25}^{81}BrO_5N^+$ [M+NH$_4$]$^+$ calcd 426.0911, found 426.0929.

Synthesis of Compound 12

A sample of methyl ketone 11 (22 mg, 0.05 mmol) was dissolved in MeOH (1 mL), cooled to −78° C. and treated with $NaBH_4$ (2 mg, 0.06 mmol). The solution was stirred for 15 minutes at same temperature to complete the reaction. Unreacted $NaBH_4$ was quenched with acetone (1 mL). Solvents were removed under reduced pressure, redissolved in $CH_2Cl_2$ (10 mL) and washed with distilled water (10 mL). The aqueous layer was extracted with $CH_2Cl_2$ (2×10 mL). Organic fractions were combined, evaporated and purified by column chromatography (5:1 petroleum ether:ethyl acetate) to yield compound 12 as a colourless oil (19 mg, 91%). 12: $R_f$ 0.14 (5:1 petroleum ether: ethyl acetate); $[\alpha]_D^{21}$=−137 (c 0.15, $CH_2Cl_2$); $^1$H-NMR: ($CDCl_3$) $δ_H$ 7.37-7.27 (complex m, 5H, Bn), 7.03 (dd, J=15.8, 4.3 Hz, 1H, H-8), 6.46 (dd, J=3.8, 1.6 Hz, 1H, H-5), 6.20 (d, J=15.7 Hz, 1H, H-9), 4.95 (m, 1H, H-7), 4.61 (d, J=12.1 Hz, 2H, $PhCH_2$), 4.56 (d, J=12.0 Hz, 2H, $PhCH_2$), 4.39 (m, 1H, H-3), 4.23 (q, J=7.0 Hz, 2H, OEt), 4.14-4.06 (complex m, 2H, H-2 and H-6), 1.32-1.24 (complex m, 6H, H-1 and OEt); $^{13}$C-NMR: ($CDCl_3$) $δ_C$ 166.2 (C, C-10), 142.8 (CH, C-8), 137.5 (C, Bn), 129.5 (CH, C-5), 128.49 (CH, Bn), 128.08 (CH, Bn), 127.88 (CH, Bn), 124.1 (C, C-4), 123.2 (CH, C-9), 78.5 (CH, C-2), 72.9 (CH, C-7), 72.0 (CH, C-6), 71.1 ($CH_2$, $PhCH_2$), 68.0 (CH, C-3), 60.7 ($CH_2$, OEt), 19.3 ($CH_3$, C-1), 14.1 ($CH_3$, OEt); IR (film from $CH_2Cl_2$) $v_{max}$ 3572, 3458, 2983, 2926, 1650, 1447, 1414, 1331, 1121, 1042, 968, 852, 822, 764, 731 cm$^{-1}$; HRMS: m/z $C_{19}H_{27}^{81}BrNO_5^+$ [M+NH$_4$]$^+$ calcd 428.1073, found 428.1078.

Synthesis of Compound 13

A sample of E-ethyl ester 12 (20 mg, 0.05 mmol) was dissolved in 1,4-dioxane (1 mL). Then XantPhos (5.6 mg, 9.72×10$^{-3}$ mmol, 20%), palladium acetate (2 mg, 9.72×10$^{-3}$ mmol, 20%), sodium carbonate (25 mg, 0.24 mmol), TBAI (3 mg, 9.72×10$^{-3}$ mmol) and triethylamine (68 µL, 0.49 mmol) were added accordingly. This mixture was bubbled with CO for a few minutes to saturate the solution with CO. Then the flask was connected to a reflux condenser and placed under an atmosphere of CO (balloon). The whole set-up was evacuated and purged with CO three times and stirred vigorously at 95° C. for 2.5 hours. Then the solution was diluted with dichloromethane (5 mL) and filtered through a silica plug. The crude product was purified by column chromatography (3:1 petroleum ether:ethyl acetate) to yield lactone 13 as a colourless oil (8 mg, 46%). 13: $R_f$ 0.24 (3:1 petroleum ether: ethyl acetate); $[\alpha]_D^{20}$=−234 (c 0.3, CHCl$_3$); $^1$H-NMR: (CDCl$_3$) δ$_H$ 7.38-7.29 (complex m, 5H, Bn), 7.13 (dd, J=4.3, 3.7 Hz, 1H, H-5), 7.06 (dd, J=15.8, 5.4 Hz, 1H, H-8), 6.23 (dd, J=15.9, 1.2 Hz, 1H, H-9), 5.08 (m, 1H, H-3), 4.86 (quintet, J=6.8 Hz, 1H, H-2), 4.65 (d, J=12.2 Hz, 2H, PhCH$_2$), 4.54 (d, J=12.2 Hz, 2H, PhCH$_2$), 4.39 (m, 1H, H-7), 4.28 (apparent t, J=3.6 Hz 1H, H-6), 4.24 (q, J=7.1 Hz, 2H, OEt), 1.32 (t, J=7.2 Hz, 3H, OEt), 1.24 (d, J=6.6 Hz, 3H, H-1); $^{13}$C-NMR: (CDCl$_3$) δ$_C$ 166.0 (C, C-10), 165.8 (C, C-13), 141.9 (CH, C-8), 137.0 (C, Bn), 134.2 (CH, C-5), 132.2 (C, C-4), 128.63 (CH, Bn), 128.27 (CH, Bn), 127.85 (CH, Bn), 124.9 (CH, C-9), 77.9 (CH, C-2), 74.3 (CH, C-7), 71.8 (CH$_2$, PhCH$_2$), 70.5 (CH, C-3), 69.5 (CH, C-6), 60.7 (CH$_2$, OEt), 15.3 (CH$_3$, C-1), 14.2 (CH$_3$, OEt); IR (film from Et$_2$O) ν$_{max}$ 2980, 2959, 2926, 1714, 1662, 1447, 1439, 1384, 1302, 1266, 1180, 1039, 977, 915, 825, 726, 694, 666 cm$^{-1}$; HRMS: m/z C$_{20}$H$_{26}$NO$_6^+$ [M+NH$_4$]$^+$ calcd 376.1760, found 376.1768.

Synthesis of Compound 14

To a solution of benzyl-protected furopyrone 13 (8.0 mg, 0.02 mmol) in CH$_2$Cl$_2$ (1 mL) was added TiCl$_4$ (7.4 µL, 0.07 mmol) in CH$_2$Cl$_2$ (0.1 mL) at 0° C. After stirring at the same temperature for 10 min, the reaction was quenched with saturated aqueous NaHCO$_3$ (5 mL), and the organic layer was separated and extracted with CH$_2$Cl$_2$ (2×5 mL). The organic layers were combined and dried over anhydrous MgSO$_4$. After filtration and concentration under reduced pressure, the crude product was purified by column chromatography (2:1 petroleum ether: ethyl acetate) to yield, as a pale yellow oil, (E)-TAN-2483B ethyl ester 14 (3 mg, 56%). 14: R$_f$ 0.33 (1:1 petroleum ether: ethyl acetate); [α]$_D^{22}$=−100 (c 0.1, Et$_2$O); $^1$H-NMR: (CDCl$_3$) δ$_H$ 7.17 (dd, J=5.6, 3.3 Hz, 1H, H-5), 7.02 (dd, J=15.7, 5.2 Hz, 1H, H-8), 6.29 (dd, J=15.7, 1.7 Hz, 1H, H-9), 5.13 (dd, J=7.7, 3.1 Hz, 1H, H-3), 4.81 (quintet, J=7.0 Hz, 1H, H-2), 4.56 (m, 1H, H-6), 4.41 (m, 1H, H-7), 4.23 (q, J=7.1 Hz, 2H, OEt), 1.31 (t, J=7.2 Hz, 3H, OEt), 1.28 (d, J=6.6 Hz, 3H, H-1); $^{13}$C-NMR: (CDCl$_3$) δ$_C$ 165.9 (C, C-13), 165.8 (C, C-10), 141.2 (CH, C-8), 134.8 (CH, C-5), 131.6 (C, C-4), 125.4 (CH, C-9), 77.9 (CH, C-2), 75.1 (CH, C-7), 70.8 (CH, C-3), 63.5 (CH, C-6), 60.8 (CH$_2$, OEt), 15.3 (CH$_3$, C-1), 14.2 (CH$_3$, OEt); IR (film from CDCl$_3$) ν$_{max}$ 3760, 3672, 3644, 3447, 2983, 2929, 1663, 1448, 1370, 1096, 980, 942, 916, 869, 826, 730, 699, 667 cm$^{-1}$; HRMS: m/z C$_{13}$H$_{20}$O$_6$N$^+$ [M+NH$_4$]$^+$ calcd 286.1285, found 286.1290.

Example 3: Hydroxy-TAN-2483B (19)

Synthesis of Compound 15

Diol 4 (58 mg, 0.14 mmol) was dissolved in a solution of 20% v/v methanol in dichloromethane (5 mL) and treated with potassium carbonate (94 mg, 0.68 mmol). The solution was stirred at room temperature until the reaction was complete according to TLC analysis. The reaction mixture was filtered, treated with brine (10 mL) and extracted with dichloromethane (3×5 mL). The organic fractions were combined, dried over anhydrous MgSO$_4$ and evaporated quickly on rotary evaporator (Note: the water bath temperature of the rotary evaporator must be kept close to room temperature to avoid degradation). The crude diol was redissolved in 5 mL of THF and treated with NaIO$_4$ (145 mg, 0.68 mmol) and stirred one hour at room temperature. Reaction was quenched with 5 mL of brine after starting material has been completely consumed. Then it was extracted into diethyl ether (3×5 mL) and organic layer was dried and evaporated on rotary evaporator. The crude aldehyde was redissolved in dry THF (2 mL) and treated with (triphenylphosphoranylidene)acetaldehyde (42 mg, 0.13 mmol) and stirred overnight at room temperature. The excess solvents in the crude mixture were evaporated and the residue purified by column chromatography (5:1 petroleum ether: ethyl acetate) to obtain 15 as a colourless oil (20 mg, 42% over three steps). 15: R$_f$ 0.18 (5:1 petroleum ether:ethyl acetate); [α]$_D^{21}$=−98 (c 1.7, CH$_2$Cl$_2$); $^1$H NMR: (CDCl$_3$) δ$_H$ 9.60 (d, J=7.5 Hz, 1H, H-10), 7.38-7.27 (complex m, 5H, Bn), 6.81 (dd, J=15.9, 4.1 Hz, 1H, H-8), 6.44 (ddd, J=15.8, 7.8, 1.9 Hz, 1H, H-9), 6.39 (dd, J=5.4, 1.2 Hz, 1H, H-5), 5.12 (d, J=1.7 Hz, 1H, H-3), 4.83 (complex m, 1H, H-7), 4.63 (d, J=11.9 Hz, 1H, PhCH$_2$), 4.50 (d, J=11.7 Hz, 1H, PhCH$_2$), 3.99 (dd, J=5.4, 3.0 Hz, 1H, H-6), 2.55 (d, J=2.1 Hz, 1H, H-1); $^{13}$C NMR: (CDCl$_3$) δ$_C$ 192.9 (CH, C-10), 151.0 (CH, C-8), 137.2 (C, Bn), 132.7 (CH, C-9), 128.59 (CH, Bn), 128.21 (CH, Bn), 128.00 (CH, Bn), 126.3 (CH, C-5), 125.1 (C, C-4), 77.7 (CH, C-2), 75.6 (C, C-1), 72.2 (CH, C-7), 70.8 (CH$_2$, PhCH$_2$ and CH, C-6), 69.1 (CH, C-3); IR (film from CDCl$_3$) ν$_{max}$ 2733, 2217, 2154, 1722, 1646, 1496, 1367, 1301, 1209, 848 cm$^{-1}$; HRMS: m/z C$_{17}$H$_{21}^{81}$BrO$_3$N$^+$ [M+NH$_4$]$^+$ calcd 364.0543, found 364.0528.

Synthesis of Compound 16

A sample of alkyne 15 (20 mg, 0.06 mmol) was dissolved in THF (0.5 mL). HgSO$_4$ in H$_2$SO$_4$ (10% aqueous solution, 0.5 mL, 3 mg, 0.012 mmol) was added to this solution. The reaction mixture was stirred at room temperature for 4 hours. The mixture was diluted with Et$_2$O (5 mL) and carefully neutralized with NaHCO$_3$ powder until pH=7 was reached. The aqueous layer was washed with Et$_2$O (3×5 mL). The organic layers were combined and dried over MgSO$_4$. The crude product was chromatographed (3:1 petroleum ether: ethyl acetate) to yield the product 16 as a clear oil (16 mg, 76%). 16: R$_f$ 0.37 (3:1 petroleum ether: ethyl acetate); [α]$_D^{19}$=−126.9 (c 0.52, CH$_2$Cl$_2$); $^1$H NMR: (CDCl$_3$) δ$_H$ 9.58 (d, J=7.6 Hz, 1H, H-10), 7.37-7.27 (complex m, 5H, Bn), 6.77 (dd, J=15.8, 4.1 Hz, 1H, H-8), 6.53 (dd, J=4.9, 1.4 Hz, 1H, H-5), 6.42 (ddd, J=16.0, 7.8, 2.0 Hz, 1H, H-9), 4.84 (s, H, 1H, H-3), 4.63 (complex m, J=11.9 Hz, 2H, PhCH$_2$ and H-7), 4.52 (d, J=12.0 Hz, 1H, PhCH$_2$), 4.06 (dd, J=4.9, 1.7 Hz, 1H, H-6), 2.34 (s, 3H, H-1); $^{13}$C NMR: (CDCl$_3$) δ$_C$ 202.4 (C, C-2), 192.9 (CH, C-10), 150.6 (CH, C-8), 137.1 (C, Bn), 132.9 (CH, C-9), 128.62 (CH, Bn), 128.29 (CH, Bn), 128.0 (CH, Bn), 127.0 (CH, C-5), 121.3 (C, C-4), 80.7 (CH, C-3), 72.8 (CH, C-7), 71.1 (CH, C-6 and CH$_2$, PhCH$_2$), 28.4 (CH$_3$, C-1); IR (film from CDCl$_3$) ν$_{max}$ 2958, 2930, 2871, 2733, 2360, 2341, 1881, 1648, 1551, 1496, 1418, 1273, 1208, 1170, 1144, 861, 790, 620 cm$^{-1}$; HRMS: m/z C$_{17}$H$_{21}^{81}$BrO$_4$N$^+$ [M+NH$_4$]$^+$ calcd 382.0654, found 382.0646.

Synthesis of Compound 17

CeCl$_3$.7H$_2$O (16 mg, 0.0301 mmol) was added to a solution of ketoaldehyde 16 (16 mg, 0.0301 mmol) in CH$_2$Cl$_2$/EtOH (0.6 mL of a 1:1 v/v mixture) maintained at room temperature. This mixture was then cooled to −78° C., treated with NaBH$_4$ (5.8 mg, 0.15 mmol) in EtOH (0.3 mL) and stirring continued at −78° C. for one hour. After this time TLC analysis (1:3 ethyl acetate:petroleum ether) showed the absence of starting material. Then 0.5 mL of acetone was added, concentrated under reduced pressure to give yellow oil. This material was purified by flash chromatography (1:1 petroleum ether: ethyl acetate) to obtain 17 as a colourless oil (14 mg, 93%). 17: R$_f$ 0.24 (1:1 petroleum ether: ethyl acetate); [α]$_D^{24}$=−16.6 (c 0.15, CH$_2$Cl$_2$); $^1$H-NMR: (CDCl$_3$) δ$_H$ 7.36-7.28 (complex m, 5H, Bn), 6.42 (dd, J=3.4, 1.8 Hz, 1H, H-5), 6.07 (dt, J=15.7, 5.3 Hz, 1H, H-9), 5.93 (dd, J=15.9, 6.4 Hz, 1H, H-8), 4.75 (apparent t, J=5.4 Hz, 1H, H-7), 4.62 (d, J=11.9 Hz, 2H, PhCH$_2$), 4.56 (d, J=11.9 Hz, 2H, PhCH$_2$), 4.36 (complex m, 1H, H-2), 4.21 (d, J=4.9 Hz, 2H, H-10), 4.08 (dd, J=4.8, 1.9 Hz, 1H, H-6), 4.03 (d, J=2.0 Hz, 1H, H-3), 1.32 (d, 3H, J=5.6 Hz, H-1); $^{13}$C-NMR: (CDCl$_3$) $\delta_C$ 137.7 (C, Bn), 134.5 (CH, C-9), 130.2 (CH, C-5), 128.48 (CH, Bn), 128.95 (CH, Bn), 127.83 (CH, Bn), 125.8 (CH, C-8), 123.3 (C, C-4), 77.7 (CH, C-3), 73.5 (CH, C-7), 72.9 (CH, C-6), 71.1 (CH$_2$, PhCH$_2$), 67.7 (CH, C-2), 63.1 (CH$_2$, C-10), 19.5 (CH$_3$, C-1); IR (film from CDCl$_3$) $\nu_{max}$ 3628, 3381, 3033, 2927, 2630, 2339, 1646, 1455, 1345, 1071, 913, 857, 735, 698, 626 cm$^{-1}$; HRMS: m/z C$_{17}$H$_{25}$$^{81}$BrO$_4$N$^+$ [M+NH$_4$]$^+$ calcd 386.0961, found 386.0949.

Synthesis of Compound 18

A sample of diol 17 (45 mg, 0.12 mmol) was dissolved in 1 mL of 1,4-dioxane. Then XantPhos (14 mg, 0.0243 mmol, 20%), palladium acetate (6 mg, 0.0243 mmol, 20%), sodium carbonate (65 mg, 0.61 mmol), TBAI (9 mg, 0.0243 mmol) and triethylamine (303 µL, 1.2 mmol) were added sequentially. Then this mixture was bubbled with CO for a few minutes to saturate the solution with CO. Then the flask was connected to a reflux condenser and placed under an atmosphere of CO (balloon). The whole set-up was evacuated and purged with CO three times and stirred vigorously at 95° C. for one day. Then the solution was diluted with dichloromethane (2 mL) and filtered through a silica plug. The crude product was purified by column chromatography (1:1 petroleum ether:ethyl acetate) to yield lactone 18 as a pale yellow oil (20 mg, 52%). 18: R$_f$ 0.25 (1:1 petroleum ether: ethyl acetate); [α]$_D^{21}$=−60.6 (c 0.15, CH$_2$Cl$_2$); $^1$H-NMR: (CDCl$_3$) $\delta_H$ 7.38-7.31 (complex m, 5H, Bn), 7.07 (dd, J=7.8, 3.1 Hz, 1H, H-5), 6.09 (dt, J=15.7, 4.7 Hz, 1H, H-9), 6.03 (dd, J=15.7, 6.9 Hz, 1H, H-8), 5.03 (dd, J=7.9, 3.3 Hz, 1H, H-3), 4.83 (quintet, J=6.8 Hz, 1H, H-2), 4.62 (d, J=11.6 Hz, 2H, PhCH$_2$), 4.56 (d, J=12.1 Hz, 2H, PhCH$_2$), 4.37 (dd, J=6.6, 3.8 Hz, 1H, H-7), 4.25 (dd, J=6.2, 4.2 Hz, 1H, H-6), 4.22 (broad d, J=3.8 Hz, 2H, H-10), 1.24 (d, 3H, J=6.4 Hz, H-1); $^{13}$C-NMR: (CDCl$_3$) $\delta_C$ 166.2 (C, C-11), 137.3 (C, Bn), 135.7 (CH, C-9), 134.6 (CH, C-5), 131.5 (CH, C-4), 128.57 (CH, Bn), 128.17 (CH, Bn), 127.84 (CH, Bn), 125.6 (C, C-8), 77.8 (CH, C-2), 75.3 (CH, C-7), 71.6 (CH$_2$, PhCH$_2$), 70.4 (CH, C-6), 70.0 (CH, C-3), 62.9 (CH$_2$, C-10), 15.3 (CH$_3$, C-1); IR (film from CDCl$_3$) $\nu_{max}$ 3628, 3381, 3033, 2927, 1650, 1413, 1386, 1298, 1096, 829, 736, 689, 632 cm$^{-1}$; HRMS: m/z C$_{18}$H$_{18}$O$_5$Na$^+$ [M+Na—H$_2$O]$^+$ calcd 321.1097, found 321.1094.

Synthesis of Compound 19

To a solution of lactone 18 (5.0 mg, 0.016 mmol) in CH$_2$Cl$_2$ (0.5 mL) was added TiCl$_4$ (5.2 µL, 0.047 mmol) in CH$_2$Cl$_2$ (0.1 mL) at 0° C. After stirring at the same temperature for 10 min, the reaction was quenched with saturated aqueous NaHCO$_3$ (2 mL), and the organic layer was separated and extracted with CH$_2$Cl$_2$ (3×5 mL). The organic layers were combined and dried over anhydrous MgSO$_4$. After filtration and concentration under reduced pressure, the crude product was purified by column chromatography (ethyl acetate) to yield hydroxy-TAN-2483B 19 as a colourless oil (2.6 mg, 72%). 19: R$_f$ 0.28 (ethyl acetate); [α]$_D^{21}$=−140 (c 0.05, Et$_2$O); $^1$H-NMR: (CDCl$_3$) O$_H$ 7.09 (dd, J=7.5, 3.5 Hz, 1H, H-5), 6.17 (dt, J=15.6, 4.6 Hz, 1H, H-9), 5.98 (dd, J=15.5, 7.0 Hz, 1H, H-8), 5.07 (apparent dt, J=6.4 Hz, 1H, H-3), 4.84 (quintet, J=6.8 Hz, 1H, H-2), 4.49 (m, 1H, H-6), 4.36 (dd, J=6.8, 3.5 Hz, 1H, H-7), 4.26 (broad s, 2H, H-10), 1.27 (d, J=6.6 Hz, 3H, H-1); $^{13}$C-NMR: (CDCl$_3$) $\delta_C$ 166.3 (C, C-11), 136.5 (CH, C-9), 135.4 (CH, C-5), 131.3 (C, C-4), 124.3 (CH, C-8), 77.8 (CH, C-2), 76.2 (CH, C-7), 70.2 (CH, C-3), 64.2 (CH, C-6), 62.6 (CH$_2$, C-10), 15.3 (CH$_3$, C-1); IR (film from Et$_2$O) $\nu_{max}$ 3701, 3379, 2983, 2870, 2362, 2340, 1755, 1691, 1448, 1358, 1332, 1262, 1195, 1141, 1095, 1041, 975, 915, 825, 790, 758, 631, 616 cm$^{-1}$; HRMS: m/z C$_{11}$H$_{18}$O$_5$N$^+$ [M+NH$_4$]$^+$ calcd 244.1179, found 244.1186.

Example 4: (−)-TAN-2483B Z-ethyl ester acetate (20)

Synthesis of Compound 20

To a solution of lactone 10 (3 mg, 0.01 mmol) in CH$_2$Cl$_2$ (0.01 mL) was added acetic anhydride (10.5 µL, 0.1 mmol) and NEt$_3$ (8 µL, 0.06 mmol). After stirring room temperature for 5 hours, the crude reaction mixture was introduced directly to a silica-gel column (2:1 petroleum ether: ethyl acetate). The compound 20 was isolated as a colourless oil (1 mg, 32%). 20: R$_f$ 0.40 (2:1 petroleum ether: ethyl acetate); $^1$H NMR: (CDCl$_3$) $\delta_H$ 7.27 (dd, J=6.4, 3.5 Hz, 1H, H-5), 6.32 (dd, J=11.6, 7.4 Hz, 1H, H-8), 5.98 (d, J=11.7 Hz, 1H, H-9), 5.50 (dd, J=6.0, 2.2 Hz, 1H, H-6), 5.34 (d, J=7.3 Hz 1H, H-7), 5.12 (dd, J=7.6, 3.5 Hz, 1H, H-3), 4.85 (quintet, J=6.8 Hz, 1H, H-2), 4.18 (q, J=7.2 Hz, 2H, OEt), 2.05 (s, 3H, CH$_3$C(O)), 1.30-1.28 (complex m, 6H, OEt and H1); $^{13}$C NMR: (CDCl$_3$) $\delta_C$ 169.9 (C, C-10), 165.3 (C, Acetate), 165.3 (C, C-13), 143.8 (CH, C-8), 132.6 (CH, C-5), 132.5 (C, C-4), 123.0 (CH, C-9), 78.2 (CH, C-2), 71.4 (CH, C-3), 70.7 (CH, C-7), 65.2 (CH, C-6), 60.7 (CH$_2$, OEt), 22.6 (CH$_3$, Acetate), 15.3 (CH$_3$, OEt or C-1), 14.1 (CH$_3$, OEt or C-1); HRMS: m/z C$_{13}$H$_{20}$NO$_6^+$ [M+NH$_4$]$^+$ calcd 328.1391, found 328.1382.

Example 5: Hydroxy-TAN-2483B diacetate (21)

Synthesis of Compound 21

To a solution of diol 19 (3.0 mg, 0.01 mmol) in CH$_2$Cl$_2$ (0.1 mL) was added acetic anhydride (16 µL, 0.1 mmol) and triethylamine (21 µL, 0.2 mmol). After stirring at room temperature for two hours, the crude product was purified by column chromatography (gradient column, 9:1, 5:1, 2:1, 1:1 petroleum ether: ethyl acetate) to yield 21 as a colourless oil (1.5 mg, 36%). 21: R$_f$ 0.54 (1:1 petroleum ether: ethyl acetate); [α]$_D^{25}$=−320 (c 0.075, Et$_2$O); $^1$H-NMR: (CDCl$_3$) $\delta_H$ 7.03 (dd, J=4.8, 3.2 Hz, 1H, H-5), 6.01 (dt, J=15.6, 5.7 Hz, 1H, H-9), 5.91 (dd, J=15.6, 7.1 Hz, 1H, H-8), 5.42 (apparent dt, J=6.4 Hz, 1H, H-6), 5.02 (dq, J=7.8 Hz, 3.3, 1H, H-3), 4.85 (quintet, J=6.8 Hz, 1H, H-2), 4.61 (d, J=5.4 Hz, 2H, H-10), 4.51 (dd, J=7.1, 3.9, 1H, H-7), 2.09 (s, 3H, CH$_3$C(O)), 2.08 (s, 3H, CH$_3$C(O)), 1.27 (d, J=6.3 Hz, 3H, H-1); $^{13}$C-NMR: (CDCl$_3$) $\delta_C$ 170.5 (C, Acetate), 170.1 (C, Acetate), 165.7 (C, C-11), 132.8 (C, C-4), 131.9 (CH, C-5), 131.1 (CH, C-9), 127.1 (CH, C-8), 77.8 (CH, C-2), 73.9 (CH, C-7), 70.0 (CH, C-3), 65.6 (CH, C-6), 63.7 (CH$_2$, C-10), 20.9 (CH$_3$, Acetate), 20.6 (CH$_3$, Acetate), 15.3 (CH$_3$, C-1); HRMS: m/z C$_{15}$H$_{22}$O$_7$N$^+$ [M+NH$_4$]$^+$ calcd 328.1391, found 328.1402.

Example 6: Methoxy-TAN-2483B (22)

Synthesis of Compound 22

To a solution of proton sponge (33.90 mg, 0.154 mmol) in CH$_2$Cl$_2$ (0.3 mL) was added Meerwein salt (17.6 mg, 0.11 mmol). After cooling the suspension to 0° C., diol 19 (3 mg, 0.01 mmol) in CH$_2$Cl$_2$ (0.3 mL) was added. After stirring at the same temperature for one hour, the reaction was slowly warmed to room temperature and stirred for four hours. The crude reaction mixture was directly subjected to column chromatography (gradient column, 9:1, 5:1, 2:1, 1:1 petroleum ether: ethyl acetate) to yield 22 as a colourless oil (1.2 mg, 38%). 22: R$_f$ 0.13 (1:1 petroleum ether: ethyl acetate); [α]$_D^{25}$=−78.8 (c 0.06, Et$_2$O); $^1$H-NMR: (CDCl$_3$) δ$_H$ 7.09 (dd, J=4.7, 3.6 Hz, 1H, H-5), 6.08 (dt, J=15.6, 5.2 Hz, 1H, H-9), 5.94 (dd, J=15.6, 7.1 Hz, 1H, H-8), 5.07 (apparent m, 1H, H-3), 4.84 (quintet, J=6.9 Hz, 1H, H-2), 4.49 (m, 1H, H-6), 4.48 (dd, J=6.8, 3.5 Hz, 1H, H-7), 3.99 (dd, J=1.5, 0.8 Hz, 2H, H-10), 3.38 (s, 3H, OCH$_3$), 1.27 (d, J=6.3 Hz, 3H, H-1); $^{13}$C-NMR: (CDCl$_3$) δ$_C$ 169.3 (C, C-11), 135.4 (CH, C-5), 135.1 (CH, C-9), 131.3 (C, C-4), 125.5 (CH, C-8), 77.8 (CH, C-2), 76.2 (CH, C-7), 72.0 (CH$_2$, C-10), 70.2 (CH, C-3), 64.2 (CH, C-6), 58.44 (CH$_3$, OMe), 15.3 (CH$_3$, C-1); IR (film from Et$_2$O) ν$_{max}$ 2975, 2861, 1444, 1381, 1350, 1297, 1117, 1075, 1044, 934, 880, 844, 794, 499, 440 cm$^{-1}$; HRMS: m/z C$_{24}$H$_{32}$O$_{10}$N$^+$ [2M+NH$_4$]$^+$ calcd 499.2367, found 499.2381.

Example 7: Cancer Cell Growth Inhibition

HL-60, 1A9 and MCF cells were cultured at 37° C. in a 5% CO$_2$ in air atmosphere in RPMI-1640 medium supplemented with 10% fetal calf serum, 100 units/mL penicillin, and 100 units/mL streptomycin (with 0.1% insulin added to the medium for 1A9 and MCF7 cell cultures). An MTT cell proliferation assay was used that involved the reduction of 3-(4,5-dimethylthiazol-2-yl)-2,5-diphenoyltetrazolium bromide (MTT) by viable cells as previously described.[14] Cells were treated with compounds of the invention in 96-well plates (duplicate wells) for 2 days (for HL-60) or 3 days (for 1A9 or MCF7), then incubated with 5 mg/mL MTT in phosphate-buffered saline for 2 h. The blue crystals that formed were solubilised in 10% sodium dodecyl sulfate, 45% dimethylformamide and the absorbance of the solutions measured at 570 nm in a multiwell plate reader (EnSpire™ 2300 Multiplate Reader from Perkin Elmer, Waltham, USA. The half-maximal inhibitory concentration (IC$_{50}$) was calculated from a concentration-response curve using Sigma Plot software v8 (Systat Software Inc. Point Richmond, Calif.).

TABLE 2

Cancer cell line inhibition results

| Cell Line | Compound 10 (IC$_{50}$ μM) | Compound 14 (IC$_{50}$ μM) | Compound 19 (IC$_{50}$ μM) |
|---|---|---|---|
| HL-60 | 3.6 | 2.2 | 42 |
| MCF7 | 9.0 | — | — |
| 1A9 | — | 3.4 | — |

Example 8: Kinase Inhibition

Compound 10 was assessed for kinase inhibition by Life Technologies using the SelectScreen® Whole Panel ACCESS Biochemical Kinase Profiling Service. The Z'-LYTE® Screening Protocol was used to obtain the results for the following kinases: AMPK A2/B1/G1, BMX, BTK, MAPK14 (p38 alpha), PLK1, TXK. The LanthaScreen Protocol was used to obtain the result for the following kinase: NUAK2.

TABLE 2

Kinase inhibition results for compound 10

| Kinase | Inhibition (IC$_{50}$ at 10 μM) |
|---|---|
| AMPK A2/B1/G1 | 81 |
| BTK | 83 |
| PLK1 | 81 |
| BMX | 80 |
| NUAK2 | 76 |
| MAPK14 | 74 |
| TXK1 | 71 |

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

LIST OF REFERENCES

1. Krohn, K., et al., *Eur. J. Org. Chem.*, 2002, 2331-2336.
2. Qin, S., et al., *Eur. J. Org. Chem.*, 2009, 3279-3284.
3. Oh, H., et al., *Tetrahedron Lett.*, 2001, 42, 975-977.
4. Kock, I., et al., *Eur. J. Org. Chem.*, 2007, 2186-2190.
5. Krohn, K., et al., *Chirality*, 2007, 19, 464-470.
6. Japanese Patent 10287679, 1998: *Chem. Abstr.*, 1999, 130, 3122e.
7. Nozawa, O., et al., *J. Antibiot.*, 1995, 48, 113-118.
8. Nozawa, O., et al., *J. Antibiot.*, 2000, 53, 1296-1300.
9. Gao, X., et al., *Org. Lett.*, 2003, 5, 451-454.
10. Gao, X. and Snider, B. B., *J. Org. Chem.*, 2004, 69, 5517-5527.
11. Shaabani, A., et al., *Bioorg. Med. Chem. Lett.*, 2008, 18, 3968-3970.
12. Hewitt, R. J., and Harvey, J. E., *Org. Biomol. Chem.*, 2011, 9, 998-1000.
13. Kim, C., et al., *Org. Lett.*, 1999, 1, 1295-1297.
14. Hood, K. A., et al., *Apoptosis*, 2001, 6, 207-219.

The invention claimed is:

1. A method of inhibiting bone marrow tyrosine kinase (BMX) or Bruton tyrosine kinase (BTK), the method comprising contacting the BMX or the BTK with an inhibitory amount of a compound of the formula:

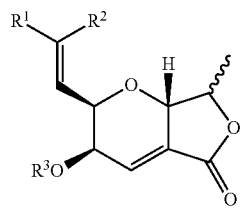

wherein
R$^1$ and R$^2$ may each be H, C$_1$-C$_6$ alkyl, C$_1$-C$_6$ alkoxy, C$_2$-C$_6$ alkenyl, C$_2$-C$_6$ alkynyl, aryl, CO$_2$H, CO$_2$alkyl, or C(=O)alkyl, wherein each alkyl, alkoxy, alkenyl, alkynyl or aryl group may optionally be substituted with OH, NH$_2$, halogen, alkoxy, acyloxy or aryl; and
R$^3$ is H, C$_1$-C$_6$ alkyl, C$_1$-C$_6$ acyl, aryl, benzyl or trialkylsilyl;

provided that $R^1$ is not $CH_3$ when $R^2$ and $R^3$ are both H or when $R^2$ is H and $R^3$ is acetyl;
or a pharmaceutically acceptable salt thereof.

2. A method as claimed in claim 1, wherein:
$R^1$ and $R^2$ may each be H, $C_1$-$C_6$ alkyl, $C_1$-$C_6$ alkoxy, $C_2$-$C_6$ alkenyl, $C_2$-$C_6$ alkynyl, aryl, $CO_2H$, $CO_2$alkyl, or C(=O)alkyl, wherein each alkyl, alkoxy, alkenyl, alkynyl or aryl group may optionally be substituted with OH, $NH_2$, halogen, or aryl; and
$R^3$ is H, $C_1$-$C_6$ alkyl, aryl, benzyl or trialkylsilyl;
provided that $R^1$ is not $CH_3$ when $R^2$ and $R^3$ are both H or when $R^2$ is H and $R^3$ is acetyl.

3. A method as claimed in claim 1, wherein one of $R^1$ and $R^2$ is $C_1$-$C_6$ alkyl and the other is H.

4. A method as claimed in claim 1, wherein one of $R^1$ and $R^2$ is $CH_2OH$ and the other is H.

5. A method as claimed in claim 1, wherein one of $R^1$ and $R^2$ is $CO_2$alkyl and the other is H.

6. A method as claimed in claim 1, wherein one of $R^1$ and $R^2$ is $CO_2H$ and the other is H.

7. A method of claim 1, wherein the compound is selected from the group consisting of

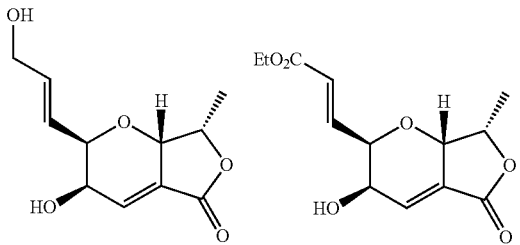

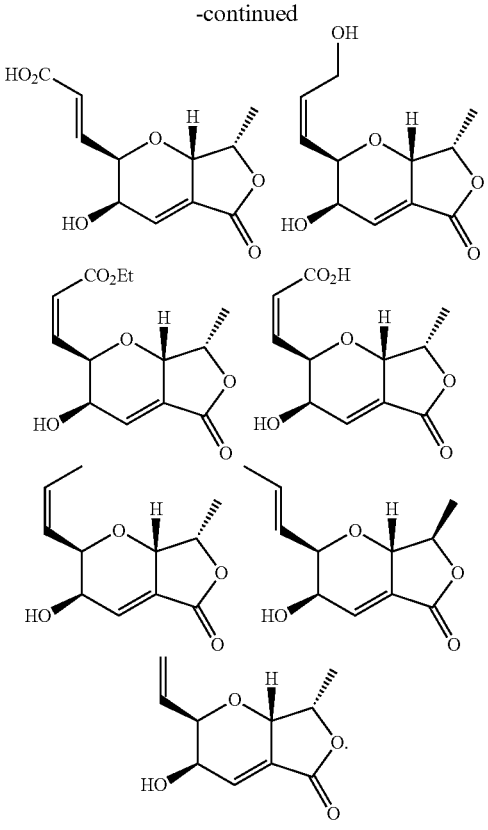

* * * * *